(12) United States Patent
Muller et al.

(10) Patent No.: US 7,276,529 B2
(45) Date of Patent: *Oct. 2, 2007

(54) METHODS OF THE TREATMENT OR PREVENTION OF EXERCISE-INDUCED ASTHMA USING (+)-2-[1-(3-ETHOXY-4-METHOXYPHENYL)-2-METHYLSULFONYLETHYL]-4-ACETYLAMINOISOINDOLINE-1,3-DIONE

(75) Inventors: George W. Muller, Bridgewater, NJ (US); Peter H. Schafer, Sommerset, NJ (US); Patricia E. W. Rohane, Florham Park, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/392,846

(22) Filed: Mar. 28, 2006

(65) Prior Publication Data

US 2006/0183788 A1    Aug. 17, 2006

Related U.S. Application Data

(60) Continuation-in-part of application No. 11/106,142, filed on Apr. 13, 2005, which is a division of application No. 10/392,195, filed on Mar. 19, 2003, now Pat. No. 6,962,940.

(60) Provisional application No. 60/438,450, filed on Jan. 7, 2003, provisional application No. 60/366,515, filed on Mar. 20, 2002.

(51) Int. Cl.
*A61K 31/4035* (2006.01)
*C07D 209/44* (2006.01)

(52) U.S. Cl. .................. 514/417; 548/478; 548/469
(58) Field of Classification Search ............. 548/478, 548/469; 514/417
See application file for complete search history.

(56) References Cited

U.S. PATENT DOCUMENTS

| | | | |
|---|---|---|---|
| 3,031,450 A | 4/1962 | Fischer et al. | |
| 3,322,755 A | 5/1967 | Roch et al. | |
| 3,920,636 A | 11/1975 | Takahashi et al. | |
| 4,001,237 A | 1/1977 | Partyka et al. | |
| 4,001,238 A | 1/1977 | Partyka et al. | |
| 4,047,404 A | 9/1977 | Hayashi | |
| 4,060,615 A | 11/1977 | Matier et al. | |
| 4,101,548 A | 7/1978 | Crenshaw et al. | |
| 4,162,316 A | 7/1979 | Nishimura et al. | |
| 4,209,623 A | 6/1980 | Juby | |
| 4,880,810 A | 11/1989 | Lowe, III | |
| 4,885,301 A | 12/1989 | Coates | |
| 5,147,875 A | 9/1992 | Coates et al. | |
| 5,354,571 A | 10/1994 | Morikawa et al. | |
| 5,401,774 A | 3/1995 | Pamukcu et al. | |
| 5,439,895 A | 8/1995 | Lee et al. | |
| 5,488,055 A | 1/1996 | Kumar et al. | |
| 5,608,914 A | 3/1997 | Keesler | |
| 5,614,530 A | 3/1997 | Kumar et al. | |
| 5,614,627 A | 3/1997 | Takase et al. | |
| 5,658,940 A | 8/1997 | Muller et al. | |
| 5,698,579 A | 12/1997 | Muller | |
| 5,703,098 A | 12/1997 | Muller et al. | |
| 5,710,170 A | 1/1998 | Guay et al. | |
| 5,728,844 A | 3/1998 | Muller et al. | |
| 5,728,845 A | 3/1998 | Muller et al. | |
| 5,736,570 A | 4/1998 | Muller et al. | |
| 5,798,373 A | 8/1998 | Warrellow | |
| 5,801,195 A | 9/1998 | Muller et al. | |
| 5,849,770 A | 12/1998 | Head et al. | |
| 5,877,200 A | 3/1999 | Muller | |
| 5,891,896 A | 4/1999 | Warrellow et al. | |
| 6,011,050 A | 1/2000 | Muller et al. | |
| 6,020,339 A | 2/2000 | Perrier et al. | |
| 6,020,358 A * | 2/2000 | Muller et al. | ............. 514/411 |
| 6,034,089 A | 3/2000 | Han et al. | |
| 6,046,221 A | 4/2000 | Muller et al. | |
| 6,069,156 A | 5/2000 | Oku et al. | |
| 6,162,830 A | 12/2000 | Connor et al. | |
| 6,166,041 A | 12/2000 | Cavalla et al. | |
| 6,177,471 B1 | 1/2001 | Menander et al. | |
| 6,204,275 B1 | 3/2001 | Friesen et al. | |
| 6,218,400 B1 | 4/2001 | Daugan et al. | |
| 6,300,335 B1 | 10/2001 | Campbell et al. | |
| 6,316,472 B1 | 11/2001 | Frenette et al. | |

(Continued)

FOREIGN PATENT DOCUMENTS

EP        0 347 146        6/1989

(Continued)

OTHER PUBLICATIONS

U.S. Appl. No. 60/454,155, filed Mar. 12, 2003, Muller, G. et al.

(Continued)

*Primary Examiner*—Rebecca Anderson
*Assistant Examiner*—Shawquia Young
(74) *Attorney, Agent, or Firm*—Jones Day

(57) ABSTRACT

Methods of treating, managing or preventing exercise-induced asthma are disclosed. Specific methods encompass the administration of (+)-2-[1-(3-ethoxy-4-methoxyphenyl)-2-methylsulfonylethyl]-4-acetylaminoisoindoline-1,3-dione alone or in combination with a second active agent. Pharmaceutical compositions and single unit dosage forms are also disclosed.

15 Claims, 16 Drawing Sheets

U.S. PATENT DOCUMENTS

| | | | |
|---|---|---|---|
| 6,333,354 B1 | 12/2001 | Schudt | |
| 6,962,940 B2 * | 11/2005 | Muller et al. | 514/417 |

FOREIGN PATENT DOCUMENTS

| | | |
|---|---|---|
| EP | 0 349 239 A2 | 6/1989 |
| EP | 0 351 058 | 6/1989 |
| EP | 0 352 960 A2 | 7/1989 |
| EP | 0 395 328 | 4/1990 |
| EP | 0 428 268 A2 | 10/1990 |
| EP | 0 463 756 A1 | 6/1991 |
| EP | 0 526 004 A1 | 7/1992 |
| EP | 0 607 439 A1 | 9/1992 |
| EP | 0 722 937 A1 | 1/1996 |
| EP | 0 722 943 A1 | 1/1996 |
| EP | 0 722 944 A1 | 1/1996 |
| GB | 2 063 249 A | 9/1980 |
| WO | WO93/07149 | 4/1993 |
| WO | WO93/12095 | 6/1993 |
| WO | WO94/01728 | 1/1994 |
| WO | WO94/05661 | 3/1994 |
| WO | WO94/29277 | 12/1994 |
| WO | WO95/19978 | 7/1995 |
| WO | WO96/32379 | 10/1996 |
| WO | WO97/03070 | 1/1997 |
| WO | WO97/03675 | 2/1997 |
| WO | WO97/03985 | 2/1997 |
| WO | WO97/24334 | 7/1997 |
| WO | WO98/06722 | 2/1998 |
| WO | WO98/08848 | 3/1998 |
| WO | WO98/14448 | 4/1998 |
| WO | WO98/16521 | 4/1998 |
| WO | WO98/17668 | 4/1998 |
| WO | WO98/23597 | 6/1998 |
| WO | WO98/38168 | 9/1998 |
| WO | WO99/06041 | 2/1999 |

OTHER PUBLICATIONS

U.S. Appl. No. 60/454,149, filed Mar. 12, 2003, Muller, G. et al.
U.S. Appl. No. 60/438,448, filed Jan. 7, 2003, Muller, G. et al.
U.S. Appl. No. 60/436,975, filed Dec. 30, 2002, Muller, G. et al.
U.S. Appl. No. 60/366,515, filed Mar. 20, 2002, Muller, G. et al.
Akazome, M. et al., 1997, "Asymmetric recognition of 1-arylethylamines by (R)-phenylglycyl-(R)-phenylglycine and its mechanism," Tetrahedron: Asymmetry, Elsevier Scince Publishers, Amsterdam, NL, 8(14):2331-2336.
Au et al., 1998, Brit. J. Pharm. 123:1260-1266.
Baehr et al., 1979, J. Biol. Chem. 254:11669.
Baughman et al., 1990, J. Lab. Clin. Med. 115:36-42.
Beavo and Reifsnyder, Trends in Pharm., 11, 150-55, 1990.
Bissonnette et al., 1989, Inflammation 13:329-339.
Bloom and Beavo 1996, Proc. Natl. Acad. Sci. USA 93:14188-14192.
Brackeen, M.F. et al., 1995, "Design and synthesis of conformationally constrained analogues of 4-(3-butoxy-4-methoxybenzyl) imidazolidin-2-one (Ro 20-1724) as potent inhibitors of cAMP-specific phosphodiesterase", J. Med. Chem. 38:4848-54.
Carstensen, Jens T., 1995, Drug Stability: Principles & Practice, 2nd ed., Marcel Dekker, New York, NY pp. 379-380.
Casini et al., 1964, Farmaco Ed. Sci. 19:563.
Clouse et al., 1989, J. Immunol. 142:431-438.
Derian et al., 1995, J. Immunol. 154:308-317.
Duh et al., 1989, Proc. Nat. Acad. Sci. 86:5974-5978.
Featherstone, R.L., et al., 2000, "Comparison of phosphodiesterase inhibitors of differing isoenzyme selectivity added to St. Thomas' hospital cardioplegic solution used for hypothermic preservation of rat lungs", Am J. Respir. Crit. Care Med. 162:850-6.
Gillespie et al., 1989, Mol. Pharm. 36:773.
Hidaka and Asano 1976, Biochem. Biophys. Acta 429:485.
Hinshaw et al. 1990, Circ. Shock 30:2797-292.
Holler et al. 1990, Blood 75:1011-1016.
Johnson et al., 1989, Endocrinology 124:1424-1427.
List et al., 1990, J. Clin. Oncol. 8:1424.MDS.
Luke, G.P. et al., 1999, "Synthesis of (S)-5-(1-aminoethyl)-2-(cyclohexylmethoxy) benzamide," Tetrahedron: Asymmetry, Elsevier Science Publishers, Amsterdam, NL, 10(22):4393-4403.
Merck Manual (1999) 17$^{th}$ ed., 953.
Monté et al., 1990, Blood 79:2670.
Muller, George, et al., 1999, Bioorganic & Medicinal Chemistry Letters 9; pp. 1625-1630.
Muller et al., 1998, Bioorg. & Med Chem Lett. 8:2669-2674.
Muller, et al., 1996, J. Med. Chem. 39:3238.
Nicholson et al., 1991, Trends Pharmaco. Sci. 12:19.
Shealy et al., 1965, "D- and L-thalidomide." Chem. Indus. 12;24:1030-1.
Tierney, et al., ed., 1998, Current Medical Diagnosis & Treatment, 37$^{th}$ ed., Appleton & Lange, pp. 499.
Verghese, et al., Journal of Pharmacology and Experimental Therapeutics, 272(3), 1313-1320, 1995.
Van Dullemen et al., 1995, Gastroenterology, 109:129-135.
Wilen, S.H., et al., 1977, Tetrahedron 33:2725.
Wilen, S.H., 1972, Tables of Resolving Agents and Optical Resoutions (E.L. Eliel, Ed., Univ. of Notre Dame Press, Notre Dame, IN) p. 268.
Wolff, Manfred E., ed., Burger's Medicinal Chemistry and Drug Discovery, 5th ed. 1995 172-178, 949-982.
Dredge et al., 2003, "Angiogenesis inhibitors in cancer therapy," Curr. Opin. Investig. Drugs 4(6):667-674.
Dredge et al., 2002, "Immunological effects of thalidomide and its chemical and functional analogs," Crit. Rev. Immunol. 22(5-6):425-437.
Dredge et al., 2002, "Recent developments in antiangiogenic therapy," Expert Opin. Biol. Ther. 2(8):953-966.
Gee et al., 2003, "Selective cytokine inhibitory drugs with enhanced antiangiogenic activity control tumor growth through vascular inhibition," Cancer Res. 63(23):8073-8078.
Marriott et al., 2001, "Immunotherapeutic and antitumour potential of thalidomide analogues," Expert Opin. Biol. Ther. 1(4):1-8.
Marriott et al., 2002, "Thalidomide and its analogues have distinct and opposing effects on TNF-alpha and TNFR2 during co-stimulation of both CD4(+) and CD8(+) T cells," Clin. Exp. Immunol. 130(1):75-84.
Molostvov et al., 2004, "The effects of selective cytokine inhibitory drugs (CC-10004 and CC-1088) on VEGF and IL-6 expression and apoptosis in myeloma and endothelial cell co-cultures," Br. J. Haematol.124(3):366-375.
Hough DO, Dec KL: Exercise-induced asthma and anaphylaxis: Sports Med. Sep. 1994; 18(3): 162-72 [Medline].
Kaplan, TA: Exercise challenge for exercise-induced bronchospasm. Phys. Sports Med. 1995; 23: 47-57.
Lacroix, VJ: Exercise-induced asthma. Phys. Sports Med. 1999; 27: 75-92.
McFadden ER Jr., Gilbert IA: Exercise-induced asthma. N. Engl. J. Med. May 12, 1994; 330(19): 1362-7 [Medline].
The Merck Manual 556-568 (17$^{th}$ Ed.), 1999.
Storms WW: Asthma associated with exercise: Immunol Allergy Clin. North Am. Feb. 2005; 25(1): 31-43 [Medline].

\* cited by examiner

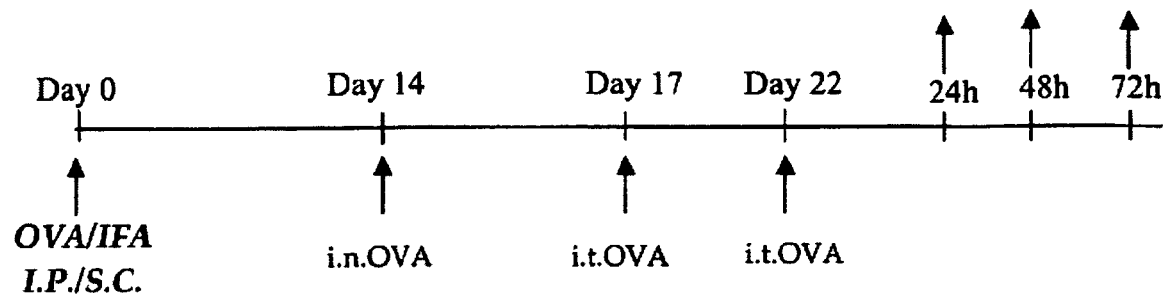
Figure 1: Time Course of sensitization protocol

Figure 2a: Inhibition of Methacholine-Induced Airway Hyper-responsiveness
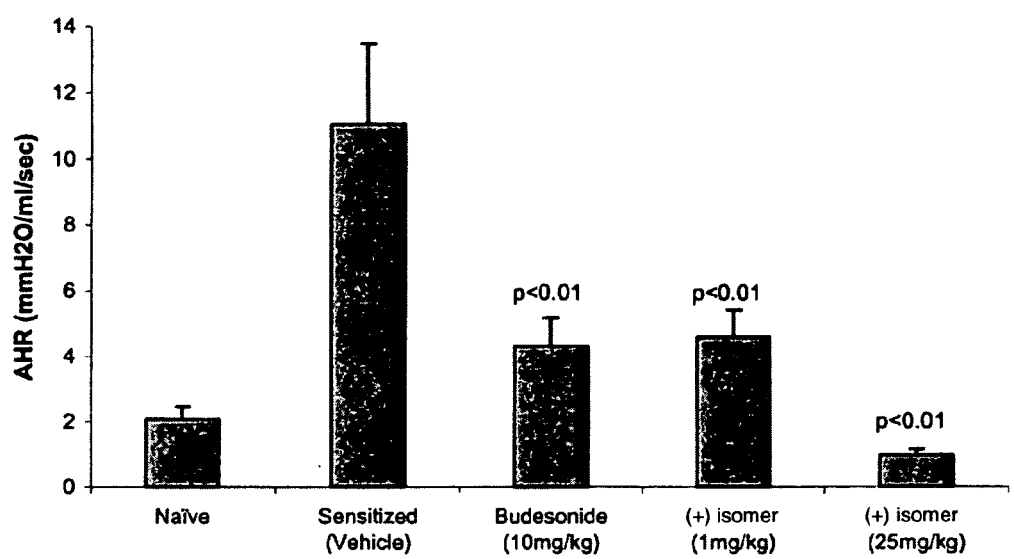
Data are expressed as mean ±SEM (n=5). p<0.01 denotes significance compared to sensitized vehicle control group. Statistical analysis by one-way ANOVA with Dunnet's post test compared to sensitized vehicle control.

Figure 2b: Time Course of Methacholine-Induced Airway Hyper-responsiveness
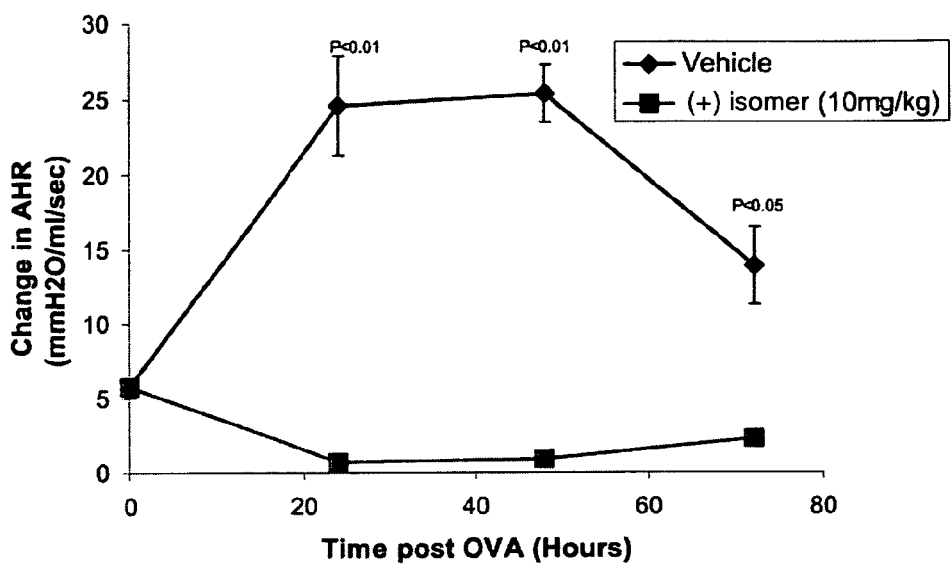
Data are expressed as mean ±SEM (n=5). p<0.01 denotes significance compared to sensitized vehicle control group. Statistical analysis by one-way ANOVA with Dunnet's post test compared to sensitized vehicle control.

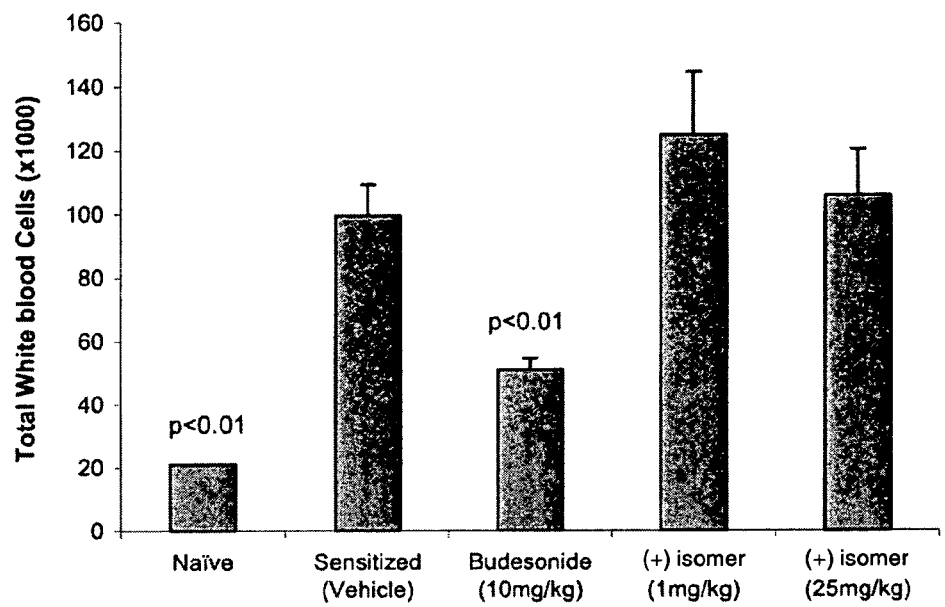
Figure 3a: Effect on Total White Blood Cell Counts 24 hour Post OVA Challenge
*Data are expressed as mean +SEM (n=5). p<0.01 denotes significance compared to sensitized vehicle control group. Statistical analysis by one-way ANOVA with Dunnet's post test compared to sensitized vehicle control.*

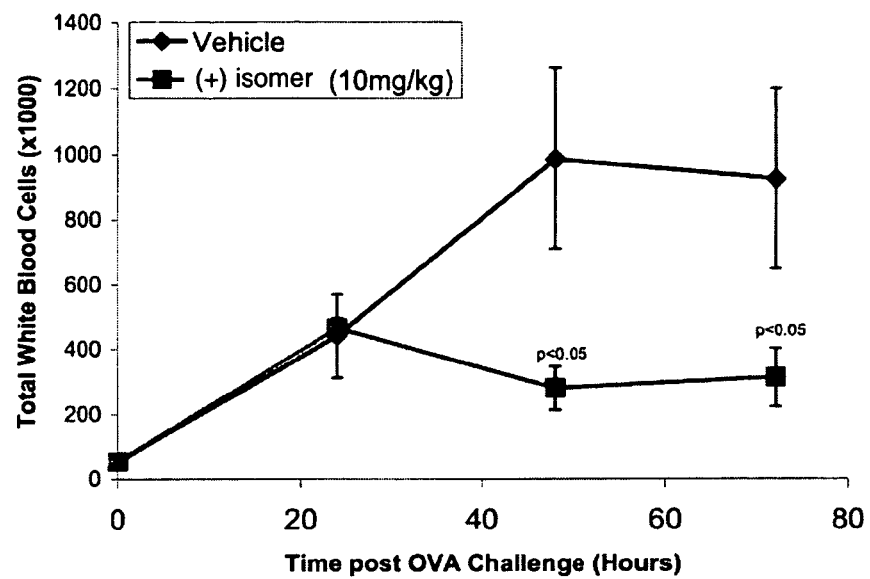
Figure 3b: Effect on the Time Course of Total White Blood Cell Infiltration into the BAL Fluid
*Data are expressed as mean +SEM (n=5). p<0.05 denotes significance compared to time matched vehicle control groups. Statistical analysis by one-way ANOVA with Bonferroni selected comparison test.*

Figure 4a: Effect on the Time Course of Total Neutrophil Counts in BAL Following OVA Challenge
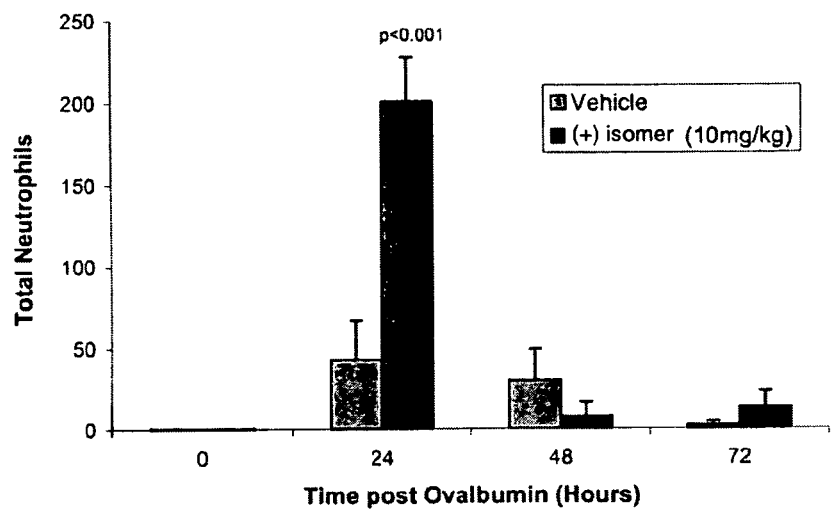
*Data are expressed as mean ±SEM (n=5). p<0.001 denotes significance compared to time matched vehicle control groups. Statistical analysis by one-way ANOVA with Bonferroni selected comparison test.*

Figure 4b: Effect on the Time Course of Total Eosinophil Counts in BAL Following OVA Challenge
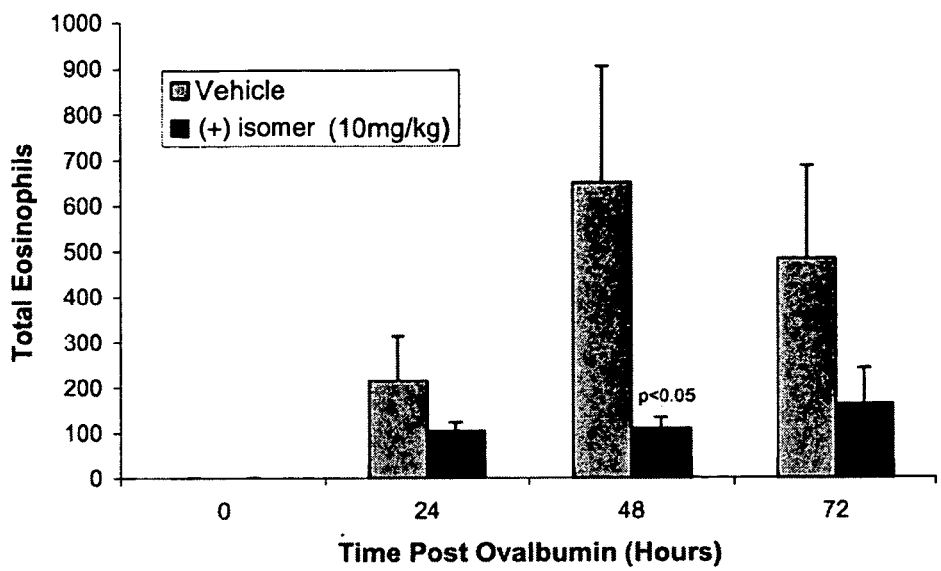
*Data are expressed as mean ±SEM (n=5). p<0.05 denotes significance compared to time matched vehicle control groups. Statistical analysis by one-way ANOVA with Bonferroni selected comparison test.*

Figure 4c: Effect on the Time Course of Total Lymphocyte Counts in BAL Following OVA Challenge
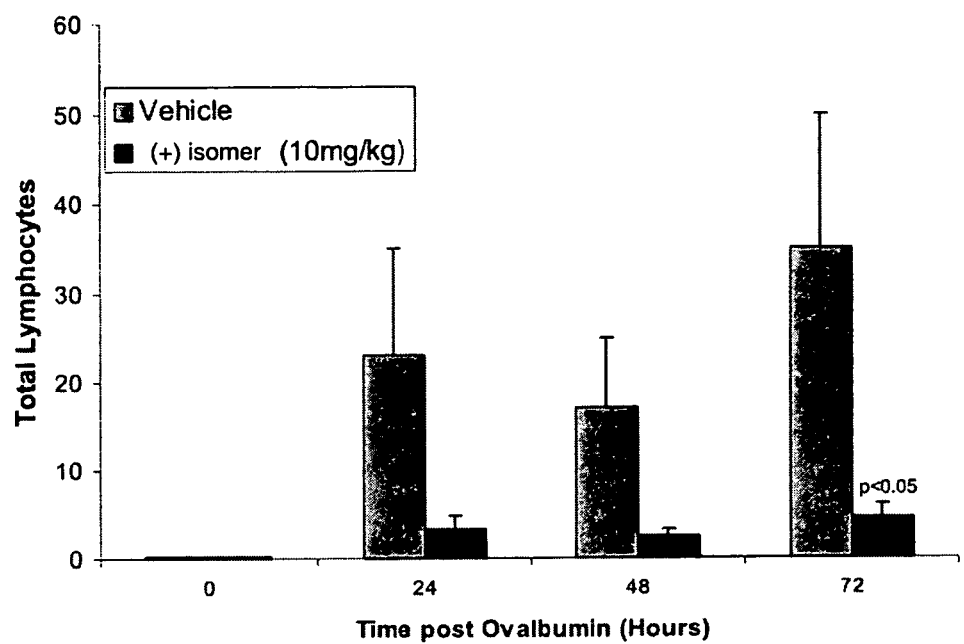
*Data are expressed as mean ±SEM (n=5). p<0.05 denotes significance compared to time matched vehicle control groups. Statistical analysis by one-way ANOVA with Bonferroni selected comparison test.*

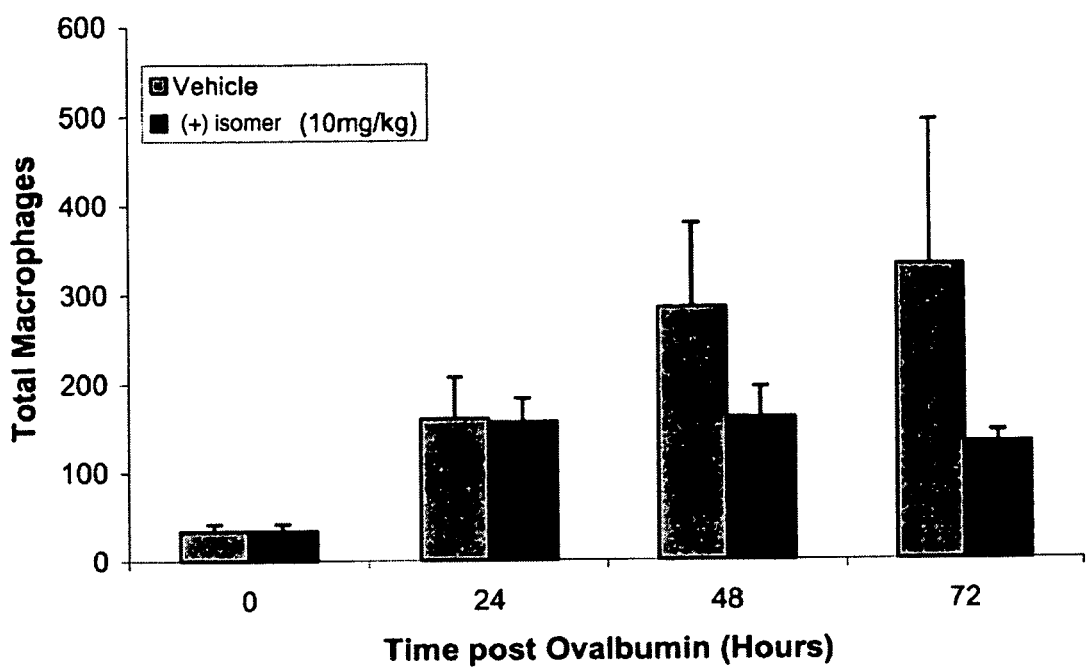
Figure 4d: Effect on the Time Course of Total Macrophage Counts in BAL Following OVA Challenge
*Data are expressed as mean ±SEM (n=5). Statistical analysis by one-way ANOVA with Bonferroni selected comparison test.*

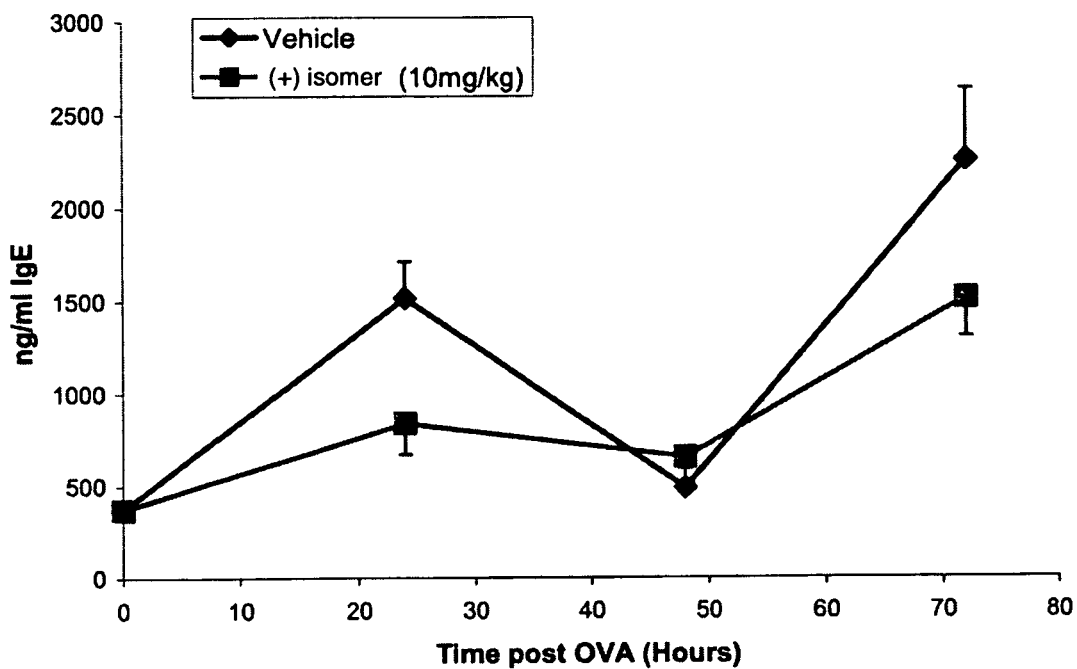
Figure 5: Effect on Total IgE Levels in Plasma Following OVA Challenge
*Data are expressed as mean ±SEM (n=5). Statistical analysis by one-way ANOVA with Bonferroni selected comparison test.*

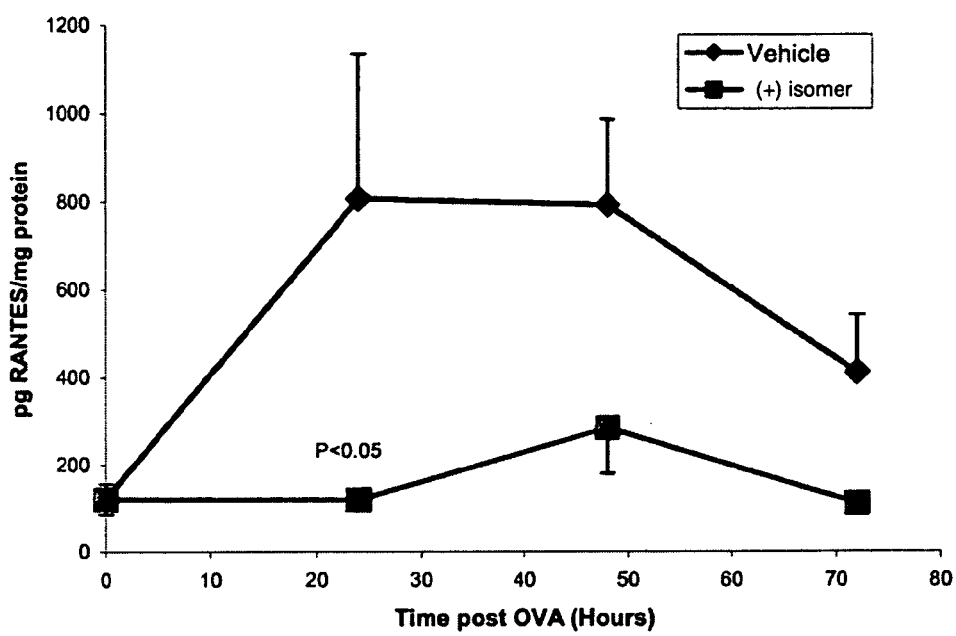
Figure 6a: Effect on Time Course of Whole Lung RANTES Level
Data are expressed as mean ±SEM (n=5). p<0.05 denotes significance compared to time matched vehicle control groups. Statistical analysis by one-way ANOVA with Bonferroni selected comparison test

Figure 6b: Effect on Time Course of Whole Lung Eotaxin Level
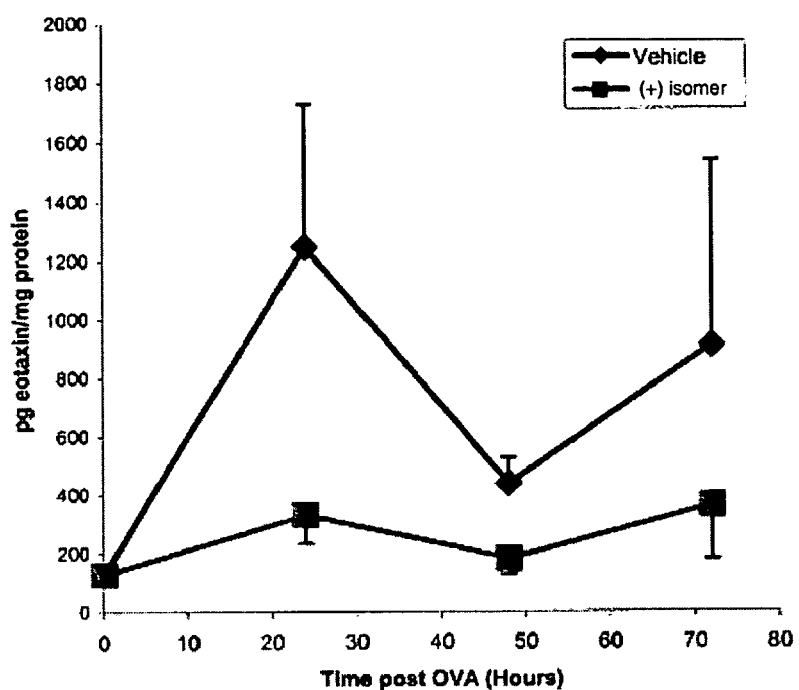
*Data are expressed as mean ±SEM (n-5). Statistical analysis by one-way ANOVA with Bonferroni selected comparison test.*

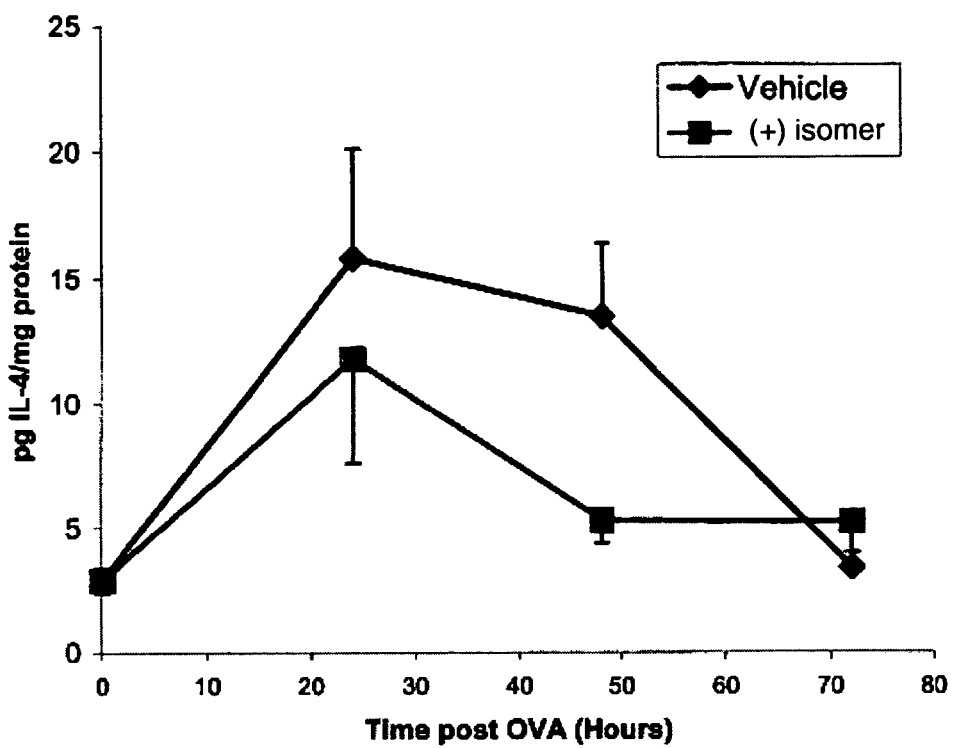
Figure 6c: Effect on Time Course of Whole Lung IL-4 Level
*Data are expressed as mean + SEM (n=5). Statistical analysis by one-way ANOVA with Bonferroni selected comparison test.*

Figure 7: Effect on PAS-Positive Airways
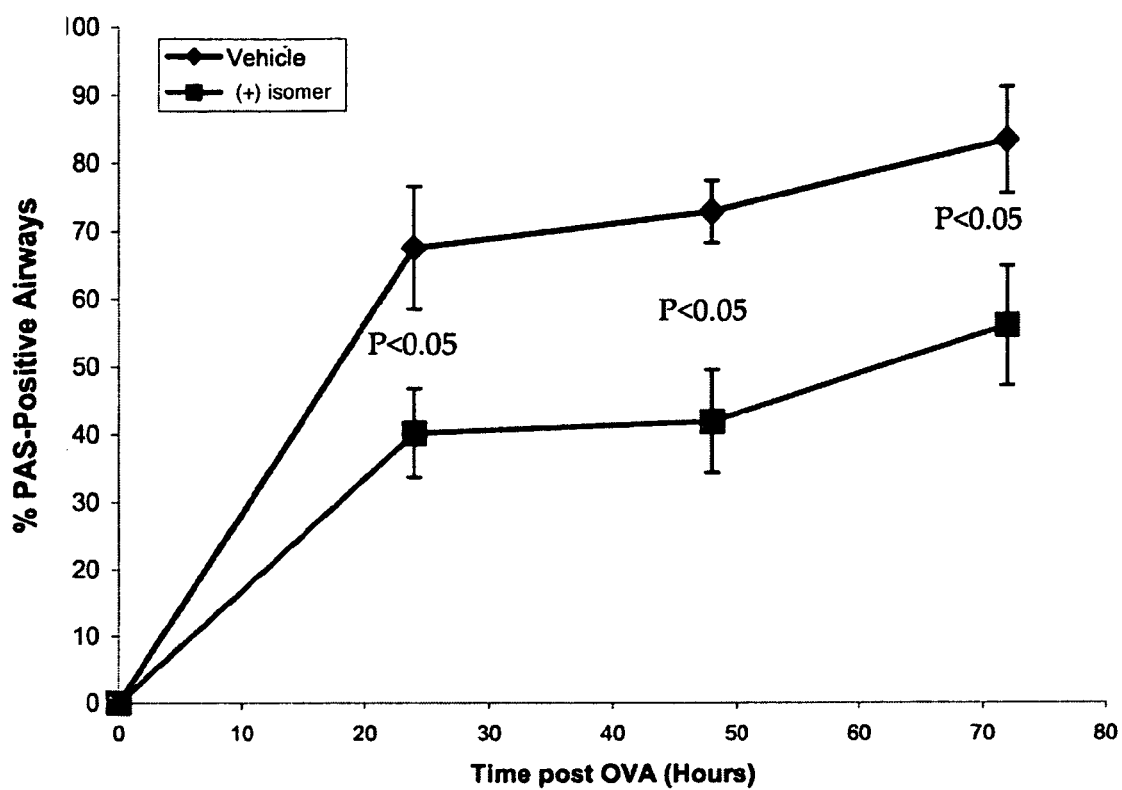
*Data are expressed as mean ± SEM (n=5). ). p<0.05 denotes significance compared to time matched vehicle control groups. Statistical analysis by one-way ANOVA with Bonferroni selected comparison test.*

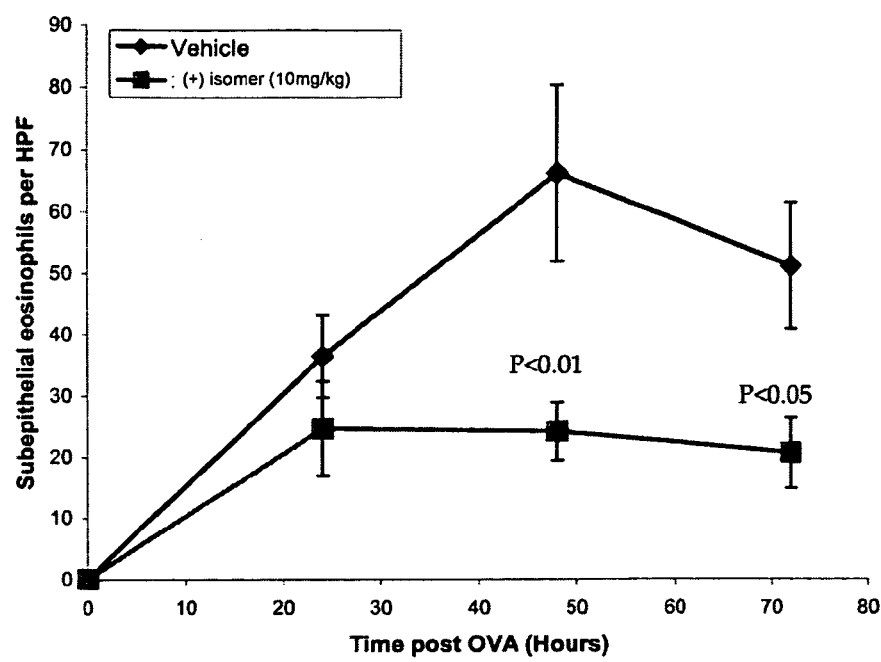
Figure 8: Effect on Subepithelial Eosinophilia
*Data are expressed as mean ± SEM (n=5). ). p<0.05 and p<0.01 denote significance compared to time matched vehicle control groups. Statistical analysis by one-way ANOVA with Bonferroni selected comparison test.*

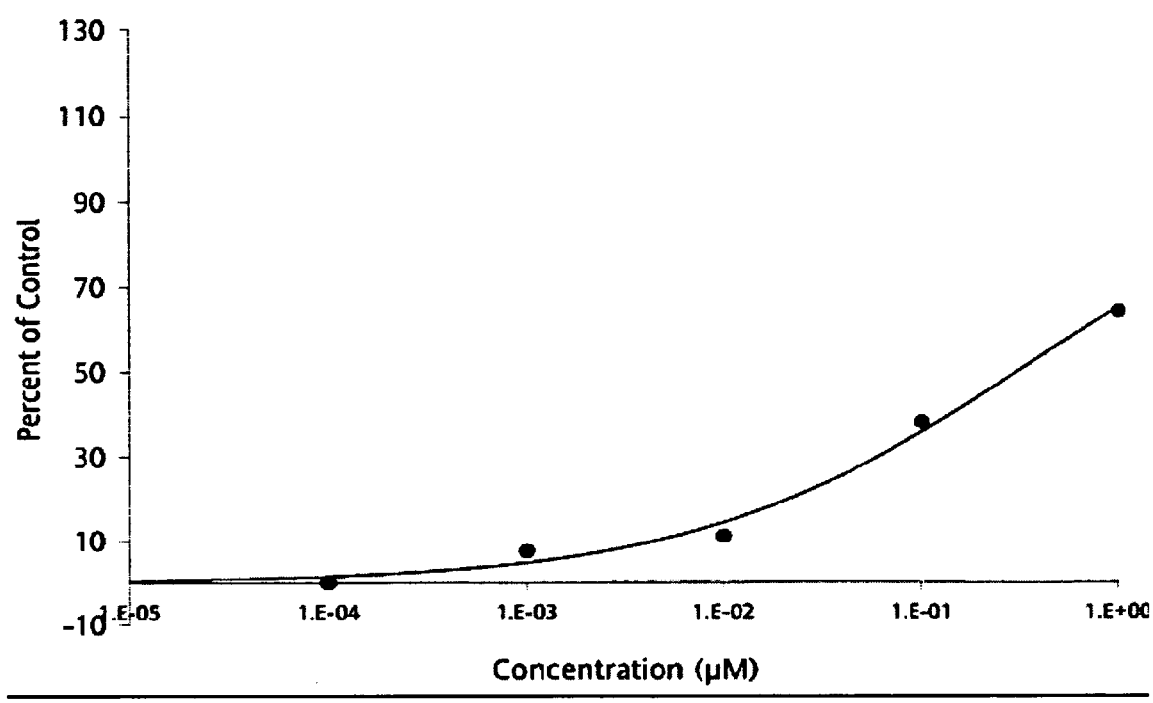
Figure 9: Concentration Response Curve

METHODS OF THE TREATMENT OR PREVENTION OF EXERCISE-INDUCED ASTHMA USING (+)-2-[1-(3-ETHOXY-4-METHOXYPHENYL)-2-METHYLSULFONYLETHYL]-4-ACETYLAMINOISOINDOLINE-1,3-DIONE

This application is a continuation-in-part of U.S. patent application Ser. No. 11/106,142, filed Apr. 13, 2005, which is a divisional of 10/392,195, filed Mar. 19, 2003, now U.S. Pat. No. 6,962,940, which claims the benefit of U.S. Provisional Application No. 60/366,515 filed Mar. 20, 2002 and U.S. Provisional Application No. 60/438,450 filed Jan. 7, 2003; and claims priority to U.S. patent application Ser. No. 11/299,702 filed Dec. 13, 2005 which claims the benefit of U.S. Provisional Application No. 60/634,982 filed Dec. 13, 2004. Each of the above is incorporated herein by reference in their entireties.

1. FIELD OF THE INVENTION

This invention provides methods of treating, preventing and/or managing exercise-induced asthma by the administration of (+)-2-[1-(3-ethoxy-4-methoxyphenyl)-2-methylsulfonylethyl]-4-acetylaminoisoindoline-1,3-dione, substantially free of its (−) enantiomer, alone or in combination with other therapeutics. The invention also provides pharmaceutical compositions and dosage forms comprising specific amounts of (+)-2-[1-(3-ethoxy-4-methoxyphenyl)-2-methylsulfonylethyl]-4-acetylaminoisoindoline-1,3-dione suitable for use in methods of treating, preventing and/or managing exercise-induced asthma.

2. BACKGROUND OF THE INVENTION

2.1 Exercise-Induced Asthma

Asthma is a pulmonary disease characterized by reversible airway obstruction, airway inflammation, and increased airway responsiveness to a variety of stimuli. *The Merck Manual*, 556-568 (17$^{th}$ ed., 1999).

Exercise-induced asthma (EIA) is a condition of respiratory difficulty that is triggered by aerobic exercise lasting several minutes. McFadden et al., Exercise-induced asthma, *N Engl J Med*, 1994 May 12; 330(19): 1362. Patients usually complain of exercise-related respiratory symptoms. This complaint is much more common among children and younger athletes but can be seen at any age. Symptoms during or following exercise include chest tightness, chest pain, cough, shortness of breath, wheezing, stomach ache and fatigue. Hough et al., Exercise-induced asthma and anaphylaxis, *Sports Med*, 1994 September; 18(3): 164; and Storms, Asthma associated with exercise, *Immunol Allergy Clin North Am*, 2005 February; 25(1): 37.

EIA affects 12-15% of the population in the United States of America. EIA is experienced by 90% of asthmatic individuals and 35-45% of people with allergic rhinitis. Even when eliminating those with rhinitis and allergic asthma, a 3-10% incidence of EIA is seen in the general population. EIA seems to be more prevalent in some winter or cold-weather sports. Some studies have demonstrated rates as high as 35% or even 50% in competitive-caliber figure skaters, ice hockey players, and cross-country skiers. Hough et al., page 163; and Lacroix, Exercise-induced asthma, *Phys Sports Med*, 1999; 27: 75.

Although the exact mechanism is unknown, there are two predominant theories as to how the symptom of EIA is triggered. Storms, page 32. One is hyperosmolarity theory or airway humidity theory, which suggests that air movement through the airway results in relative drying of the airway. Id. This in turn is believed to trigger a cascade of events that results in airway edema, secondary to hyperemia and increased perfusions in an attempt to combat the drying. This is believed to lead to the release of mediators that cause bronchoconstriction. The mediators include histamine, prostaglandin, and leukotriene. Id.

The other theory is airway rewarming theory. It is based on airway cooling and assumes that the air movement in the bronchial tree results in a decreased temperature of the bronchi, which may also trigger a hyperemic response in an effort to heat the airway. This leads to congested vessels, fluid exudation from the blood vessels into the submucosa of the airway wall, and mediator release with subsequent bronchoconstriction. Id.

Causes of EIA can be divided into the categories of medical, environmental, and drug-related. Lacroix, pages 75-92. Poorly controlled asthma or allergic rhinitis results in increased symptoms with exercise. Secretions of hay fever can aggravate EIA. Viral, bacterial, and other forms of upper respiratory infections also aggravate the symptoms of EIA. Excess of pollens or molds in the air can exacerbate EIA. Id. Pollutants such as cigarette smoke, sulfur dioxide and nitrogen oxide in the air are irritants to the airways and can lower the threshold for symptomatic bronchospasm. Id. Chemicals used in certain sports for environmental maintenance can worsen EIA symptoms. Aspirin and beta-blockers are also known as asthmatogenic agents. Id.

Still, there is a significant need for safe and effective methods of treating, preventing and managing exercise induced asthma, particularly for patients that are refractory to conventional treatments, while reducing or avoiding the toxicity and/or side effects associated with conventional therapies.

3. SUMMARY OF THE INVENTION

In one aspect, the invention provides methods of treating, preventing and/or managing exercise-induced asthma in humans in need thereof. The methods comprise administering to a patient in need of such treatment, prevention or management a therapeutically or prophylactically effective amount of (+)-2-[1-(3-ethoxy-4-methoxyphenyl)-2-methylsulfonylethyl]-4-acetylaminoisoindoline-1,3-dione, or a pharmaceutically acceptable prodrug, metabolite, polymorph, salt, solvate (e.g., hydrate) or clathrate thereof, substantially free of its (−) enantiomer.

In some embodiments, the methods further comprise the administration of a therapeutically or prophylactically effective amount of at least a second active agent including but not limited to beta 2-agonists (e.g., albuterol), mast cell stabilizers (e.g., cromolyn sodium), corticosteroids (e.g., flunisolide), xanthine derivatives (e.g., theophylline), leukotriene receptor antagonists (e.g., zafirlukast), and adrenergic agonists (e.g., epinephrine).

In another embodiment, (+)-2-[1-(3-ethoxy-4-methoxyphenyl)-2-methylsulfonylethyl]-4-acetylaminoisoindoline-1,3-dione, or a pharmaceutically acceptable prodrug, metabolite, polymorph, salt, solvate (e.g., hydrate) or clathrate thereof is administered orally in a dosage form such as a tablet and a capsule.

In further embodiments, (+)-2-[1-(3-ethoxy-4-methoxyphenyl)-2-methylsulfonylethyl]-4-acetylaminoisoindoline-1,3-dione, or a pharmaceutically acceptable prodrug, metabolite, polymorph, salt, solvate (e.g., hydrate) or clathrate thereof is administered nasally in a dosage form such as an aerosol and a spray.

In another aspect, the invention provides pharmaceutical compositions for treating, preventing and/or managing exercise-induced asthma comprising (+)-2-[1-(3-ethoxy-4-methoxyphenyl)-2-methylsulfonylethyl]-4-acetylaminoisoindoline-1,3-dione, or a pharmaceutically acceptable prodrug, metabolite, polymorph, salt, solvate (e.g., hydrate) or clathrate thereof.

In some embodiments, the invention provides single unit dosage forms for treating, preventing and/or managing exercise-induced asthma comprising (+)-2-[1-(3-ethoxy-4-methoxyphenyl)-2-methylsulfonylethyl]-4-acetylaminoisoindoline-1,3-dione, or a pharmaceutically acceptable prodrug, metabolite, polymorph, salt, solvate (e.g., hydrate) or clathrate thereof.

4. BRIEF DESCRIPTION OF FIGURE

FIG. 1 shows time course of sensitization protocol in a murine model of ovalbumin (OVA)-induced asthma to test activities of (+)-2-[1-(3-ethoxy-4-methoxyphenyl)-2-methylsulfonylethyl]-4-acetylaminoisoindoline-1,3-dione for the treatment of exercise-induced asthma.

FIG. 2a shows inhibition of methacholine-induced airway hyper-responsiveness following treatment with budesonide or (+)-2-[1-(3-ethoxy-4-methoxyphenyl)-2-methylsulfonylethyl]-4-acetylaminoisoindoline-1,3-dione in OVA-sensitized mice.

FIG. 2b shows time course of methacholine-induced airway hyper responsiveness in OVA-sensitized mice treated with vehicle or (+)-2-[1-(3-ethoxy-4-methoxyphenyl)-2-methylsulfonylethyl]-4-acetylaminoisoindoline-1,3-dione.

FIG. 3a shows effect of (+)-2-[1-(3-ethoxy-4-methoxyphenyl)-2-methylsulfonylethyl]-4-acetylaminoisoindoline-1,3-dione or budesonide on total white blood cell counts 24 hour after OVA challenge in mice.

FIG. 3b shows effect of (+)-2-[1-(3-ethoxy-4-methoxyphenyl)-2-methylsulfonylethyl]-4-acetylaminoisoindoline-1,3-dione on the time course of total white blood cell infiltration into the BAL fluid in OVA-sensitized mice.

FIG. 4a shows effect of (+)-2-[1-(3-ethoxy-4-methoxyphenyl)-2-methylsulfonylethyl]-4-acetylaminoisoindoline-1,3-dione on the time course of total neutrophil counts in BAL following OVA challenge in mice.

FIG. 4b shows effect of (+)-2-[1-(3-ethoxy-4-methoxyphenyl)-2-methylsulfonylethyl]-4-acetylaminoisoindoline-1,3-dione on the time course of total eosinophil counts in BAL following OVA challenge in mice.

FIG. 4c shows effect of (+)-2-[1-(3-ethoxy-4-methoxyphenyl)-2-methylsulfonylethyl]-4-acetylaminoisoindoline-1,3-dione on the time course of total lymphocyte counts in BAL following OVA challenge in mice.

FIG. 4d shows effect of (+)-2-[1-(3-ethoxy-4-methoxyphenyl)-2-methylsulfonylethyl]-4-acetylaminoisoindoline-1,3-dione on the time course of total macrophage counts in BAL following OVA challenge in mice.

FIG. 5 shows effect of (+)-2-[1-(3-ethoxy-4-methoxyphenyl)-2-methylsulfonylethyl]-4-acetylaminoisoindoline-1,3-dione on total IgE levels in plasma following OVA challenge in mice.

FIG. 6a shows effect of (+)-2-[1-(3-ethoxy-4-methoxyphenyl)-2-methylsulfonylethyl]-4-acetylaminoisoindoline-1,3-dione on time course of whole lung RANTES levels in mice.

FIG. 6b shows effect of (+)-2-[1-(3-ethoxy-4-methoxyphenyl)-2-methylsulfonylethyl]-4-acetylaminoisoindoline-1,3-dione on time course of whole lung eotaxin levels in mice.

FIG. 6c shows effect of (+)-2-[1-(3-ethoxy-4-methoxyphenyl)-2-methylsulfonylethyl]-4-acetylaminoisoindoline-1,3-dione on time course of whole lung IL-4 levels in mice.

FIG. 7 shows effect of (+)-2-[1-(3-ethoxy-4-methoxyphenyl)-2-methylsulfonylethyl]-4-acetylaminoisoindoline-1,3-dione (10 mg/kg) on PAS (Periodic Acid Schiff)-positive airways in mice.

FIG. 8 shows effect of (+)-2-[1-(3-ethoxy-4-methoxyphenyl)-2-methylsulfonylethyl]-4-acetylaminoisoindoline-1,3-dione on subepithelial eosinophilia in mice.

FIG. 9 shows concentration response curve of (+)-2-[1-(3-ethoxy-4-methoxyphenyl)-2-methylsulfonylethyl]-4-acetylaminoisoindoline-1,3-dione in relaxation of guinea pig trachea under spontaneous tone contraction.

5. DETAILED DESCRIPTION OF THE INVENTION

5.1 Definitions

As used herein and unless otherwise indicated, the term "pharmaceutically acceptable salt" includes, but is not limited to, salts prepared from pharmaceutically acceptable non-toxic acids or bases including inorganic acids and bases and organic acids and bases. Suitable pharmaceutically acceptable base addition salts for the compound of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

As used herein and unless otherwise indicated, the term "hydrate" means a compound of the present invention or a salt thereof, that further includes a stoichiometric or non-stoichiometeric amount of water bound by non-covalent intermolecular forces.

As used herein and unless otherwise indicated, the term "solvate" means a solvate formed from the association of one or more solvent molecules to a compound of the present invention. The term "solvate" includes hydrates (e.g., monohydrate, dihydrate, trihydrate, tetrahydrate and the like).

As used herein and unless otherwise indicated, the term "polymorph" means solid crystalline forms of a compound of the present invention or complex thereof. Different polymorphs of the same compound can exhibit different physical, chemical and/or spectroscopic properties.

As used herein and unless otherwise specified, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of (+)-2-[1-(3-ethoxy-4-methoxyphenyl)-2-methylsulfonylethyl]-4-acetylaminoisoindoline-1,3-dione that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by 1 *Burger's Medicinal Chemistry and Drug Discovery*, 172-178, 949-982 (Manfred E. Wolff ed., 5th ed. 1995).

As used herein, and unless otherwise specified, the term "enantiomer," "stereoisomer" or "isomer" encompasses all enantiomerically/stereomerically pure and enantiomerically/stereomerically enriched compounds of this invention.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure, when the compound contains 80%, 90%, 95%, 98%, 99% or more of one stereoisomer, and 20%, 10%, 5%, 2%, 1% or less of the counter stereoisomer. "Substantially free of its (−) enantiomer" is encompassed by the present invention.

As used herein, term "adverse effect" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes but is not limited to gastric and intestinal ulcerations and erosions. The term "renal toxicities" includes but is not limited to such conditions as papillary necrosis and chronic interstitial nephritis.

As used herein, the term "patient" refers to a mammal, particularly a human. In some embodiments, the patient is a female. In further embodiments, the patient is a male. In further embodiments, the patient is a child.

As used herein, and unless otherwise specified, the terms "treat," "treating" and "treatment" contemplate an action that occurs while a patient is suffering from the specified disease or disorder, which reduces the severity or symptoms of the disease or disorder or retards or slows the progression or symptoms of the disease or disorder.

As used herein, unless otherwise specified, the terms "prevent," "preventing" and "prevention" contemplate an action that occurs before a patient begins to suffer from the specified disease or disorder, which inhibits or reduces the severity or symptoms of the disease or disorder.

As used herein, and unless otherwise indicated, the terms "manage," "managing" and "management" encompass preventing the recurrence of the specified disease or disorder in a patient who has already suffered from the disease or disorder and/or lengthening the time that a patient who has suffered from the disease or disorder remains in remission. The terms encompass modulating the threshold, development and/or duration of the disease or disorder or changing the way that a patient responds to the disease or disorder.

5.2 Methods of Treatments and Prevention

A first aspect of the invention encompasses methods of treating, managing and/or preventing exercise-induced asthma which comprises administering to a patient in need of such treatment, management or prevention a therapeutically or prophylactically effective amount of (+)-2-[1-(3-ethoxy-4-methoxyphenyl)-2-methylsulfonylethyl]-4-acetylaminoisoindoline-1,3-dione, or a pharmaceutically acceptable prodrug, metabolite, polymorph, salt, solvate or clathrate thereof. Preferably the salt or solvate, most preferably the free base of (+)-2-[1-(3-ethoxy-4-methoxyphenyl)-2-methylsulfonylethyl]-4-acetylaminoisoindoline-1,3-dione, is used in this invention.

Methods encompassed by this invention comprise administering (+)-2-[1-(3-ethoxy-4-methoxyphenyl)-2-methylsulfonylethyl]-4-acetylaminoisoindoline-1,3-dione, substantially free of its (−) enantiomer, or a pharmaceutically acceptable prodrug, metabolite, polymorph, salt, solvate or clathrate of thereof, after the onset of symptoms of exercise-induced asthma. Symptoms of exercise-induced asthma include, but are not limited to, chest tightness, chest pain, cough, shortness of breath, wheezing, stomach ache and fatigue.

Methods of this invention also encompass inhibiting or averting symptoms of exercise-induced asthma prior to the onset of symptoms by administering (+)-2-[1-(3-ethoxy-4-methoxyphenyl)-2-methylsulfonylethyl]-4-acetylaminoisoindoline-1,3-dione, or a pharmaceutically acceptable prodrug, metabolite, polymorph, salt, solvate or clathrate thereof. Patients having history of asthma or allergic rhinitis are preferred candidates for preventive regimens. Methods encompassed by this invention comprise administering (+)-2-[1-(3-ethoxy-4-methoxyphenyl)-2-methylsulfonylethyl]-4-acetylaminoisoindoline-1,3-dione, or a pharmaceutically acceptable prodrug, metabolite, polymorph, salt, solvate or clathrate thereof, to a patient (e.g., a human) suffering or likely to suffer, from exercise-induced asthma.

(+) Enantiomer of 2-[1-(3-ethoxy-4-methoxyphenyl)-2-methylsulfonylethyl]-4-acetylaminoisoindoline-1,3-dione may be used in the treatment, management or prevention of exercise-induced asthma. The magnitude of a prophylactic or therapeutic dose of a particular active ingredient of the invention in the acute or chronic management of a disease or condition will vary, however, with the nature and severity of the disease or condition, and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 1 mg to about 1,000 mg per day, given as a single once-a-day dose preferably as divided doses throughout a day. More specifically, the daily dose is administered twice, three times or four times daily in equally divided doses. Specifically, a daily dose range may be from about 5 mg to about 500 mg per day, more specifically, between about 10 mg and about 200 mg per day. Specifically, the daily dose may be administered in 5 mg, 10 mg, 15 mg, 20 mg, 25 mg, 50 mg, 100 mg or 200 mg dosage forms. In managing the patient, the therapy may be initiated at a lower dose, perhaps about 1 mg to about 25 mg, and increased if necessary up to about 200 mg to about 1,000 mg per day as either a single dose or divided doses, depending on the patient's global response. In further embodiments, the daily dose of the (+) enantiomer of 2-[1-(3-ethoxy-4-methoxyphenyl)-2-methylsulfonylethyl]-4-acetylaminoisoindoline-1,3-dione is from about 0.01 mg to about 100 mg per kg of a body weight of the patient by oral administration. In some embodiments, the daily dose of the compound is about 1 mg, 10 mg or 25 mg per kg of a body weight of a patient by oral administration. In some embodiments, the daily dose of the compound is from about 1 ug to about 100 ug by inhalation.

5.2.1 Combination Therapy with a Second Active Agent or Therapy

In particular methods encompassed by this embodiment, the (+) enantiomer of 2-[1-(3-ethoxy-4-methoxyphenyl)-2- methylsulfonylethyl]-4-acetylaminoisoindoline-1,3-dione is administered in combination with another drug ("second active agent") or method of treating, managing and/or preventing exercise-induced asthma.

The (+) enantiomer of 2-[1-(3-ethoxy-4-methoxyphenyl)-2-methylsulfonylethyl]-4-acetylaminoisoindoline-1,3-dione can be combined with one or more second active agents in methods of the invention. This invention encompasses synergistic combinations for the treatment, prevention and/or management of exercise-induced asthma. The (+) enantiomer of 2-[1-(3-ethoxy-4-methoxyphenyl)-2-methylsulfonylethyl]-4-acetylaminoisoindoline-1,3-dione can also be used to alleviate adverse or unnamed effects associated with some second active agents and conversely some second active agents can be used to alleviate adverse or unnamed effects associated with the (+) enantiomer of 2-[1-(3-ethoxy-4-methoxyphenyl)-2-methylsulfonylethyl]-4-acetylaminoisoindoline-1,3-dione.

One or more second active agents can be used in the methods of the invention together with the (+) enantiomer of 2-[1-(3-ethoxy-4-methoxyphenyl)-2-methylsulfonylethyl]-4-acetylaminoisoindoline-1,3-dione. The second active agents include, but are not limited to, beta 2-agonists (e.g., albuterol), mast cell stabilizers (e.g., cromolyn sodium), corticosteroids (e.g., flunisolide), xanthine derivatives (e.g., theophylline), leukotriene receptor antagonists (e.g., zafirlukast), and adrenergic agonists (e.g., epinephrine).

The second active agents can be administered before, after or simultaneously with the (+) enantiomer of 2-[1-(3-ethoxy-4-methoxyphenyl)-2-methylsulfonylethyl]-4-acetylaminoisoindoline-1,3-dione.

In some embodiments of interest, the second active agents may include, but are not limited to, beta 2-agonists such as, but not limited to, albuterol (Proventil®, or Ventolin®), salmeterol (Serevent®), formoterol (Foradil®), metaproterenol (Alupent®), pirbuterol (MaxAir®), and terbutaline sulfate.

In other embodiments of interest, the second active agents may include, but are not limited to, corticosteroids. Non-limiting examples of corticosteroids include, but are not limited to, budesonide (e.g., Pulmicort®), flunisolide (e.g., AeroBid Oral Aerosol Inhaler® or Nasalide Nasal Aerosol®), fluticasone (e.g., Flonase® or Flovent®) and triamcinolone (e.g., Azmacort®).

In other embodiments of interest, the second active agents may include, but are not limited to, mast cell stabilizers such as cromolyn sodium (e.g., Intal® or Nasalcrom®) and nedocromil (e.g., Tilade®).

In further embodiments of interest, the second active agents may include, but are not limited to, xanthine derivatives, such as, but not limited to, theophylline (e.g., Aminophyllin®, Theo-24® or Theolair®).

In further embodiments of interest, the second active agents may include, but are not limited to, leukotriene receptor antagonists such as zafirlukast (Accolate®), montelukast (Singulair®), and zileuton (Zyflo®).

In further embodiments of interest, the second active agents may include, but are not limited to, adrenergic agonists such as epinephrine (Adrenalin®, Bronitin®, EpiPen® or Primatene Mist®).

Administration of the (+) enantiomer of 2-[1-(3-ethoxy-4-methoxyphenyl)-2-methylsulfonylethyl]-4-acetylaminoisoindoline-1,3-dione and a second active agent to a patient can occur simultaneously or sequentially by the same or different routes of administration. The suitability of a particular route of administration employed for a particular second active agent will depend on the second active agent itself (e.g., whether it can be administered orally or nasally without decomposition prior to entering the blood stream) and the subject being treated. A particular route of administration of the (+) enantiomer of 2-[1-(3-ethoxy-4-methoxyphenyl)-2-methylsulfonylethyl]-4-acetylaminoisoindoline-1,3-dione is oral administration in dosage forms of a tablet or a capsule. Another particular route of the (+) enantiomer administration is nasal administration in dosage forms of sprays or aerosols via metered dose inhaler. Particular routes of administration for the second active agents or ingredients of the invention are known to those of ordinary skill in the art. See, e.g., *The Merck Manual,* 562-568 (17$^{th}$ ed., 1999).

The amount of second active agent administered can be determined based on the specific agent used, the subject being treated, the severity and stage of disease and the amount(s) of the (+) enantiomer of 2-[1-(3-ethoxy-4-methoxyphenyl)-2-methylsulfonylethyl]-4-acetylaminoisoindoline-1,3-dione and any optional additional second active agents concurrently administered to the patient. Those of ordinary skill in the art can determine the specific amounts according to conventional procedures known in the art. In the beginning, one can start from the amount of the second active agent that is conventionally used in the therapies and adjust the amount according to the factors described above. See, e.g., *Physician's Desk Reference* (56$^{th}$ Ed., 2004).

In one embodiment of the invention, the second active agent is administered orally, nasally, intravenously or subcutaneously and once to four times daily in an amount of from about 1 to about 1,000 mg, from about 5 to about 500 mg, from about 10 to about 350 mg or from about 50 to about 200 mg. The specific amount of the second active agent will depend on the specific agent used, the age of the subject being treated, the severity and stage of disease and the amount(s) of the (+) enantiomer of 2-[1-(3-ethoxy-4-methoxyphenyl)-2-methylsulfonylethyl]-4-acetylaminoisoindoline-1,3-dione and any optional additional second active agents concurrently administered to the patient. In one embodiment, the (+) enantiomer of 2-[1-(3-ethoxy-4-methoxyphenyl)-2-methylsulfonylethyl]-4-acetylaminoisoindoline-1,3-dione can be administered in an amount of from about 1 mg to about 1,000 mg, preferably from about 5 mg to about 500 mg, and more preferably from about 10 mg and about 200 mg orally and daily alone or in combination with a second active agent disclosed herein (see, e.g., section 5.2.1), prior to, during or after the use of conventional therapy. In another embodiment, the daily dose of the (+) enantiomer of 2-[1-(3-ethoxy-4-methoxyphenyl)-2-methylsulfonylethyl]-4-acetylaminoisoindoline-1,3-dione is from about 0.01 mg to about 100 mg per kg of a body weight of a patient.

5.3 (+)-2-[1-(3-Ethoxy-4-Methoxyphenyl)-2-Methylsulfonyl Ethyl]-4-Acetylaminoisoindoline-1,3-Dione The present invention provides methods of treating, managing or preventing exercise-induced asthma, which comprises administering to a patient in need of such treatment, management or prevention a therapeutically or prophylactically effective amount of the (+) enantiomer of 2-[1-(3-ethoxy-4-methoxyphenyl)-2-methylsulfonylethyl]-4-acetylaminoisoindoline-1,3-dione, or a pharmaceutically acceptable prodrug, metabolite, polymorph, salt, solvate or clathrate thereof. Without being limited by theory, the (+) enantiomer of 2-[1-(3-ethoxy-4-methoxyphenyl)-2-methylsulfonylethyl]-4-acetylaminoisoindoline-1,3-dione is believed to be (S)-{2-[1-(3-ethoxy-4-methoxyphenyl)-2- methylsulfonylethyl]-4-acetylaminoisoindoline-1,3-dione}, which has the following structure:

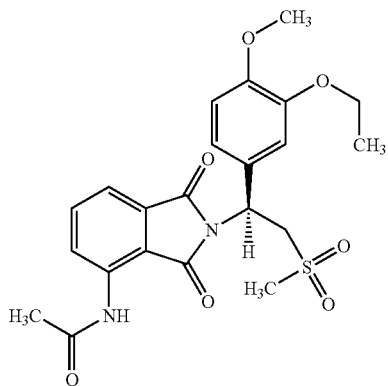

(+) Enantiomer of 2-[1-(3-ethoxy-4-methoxyphenyl)-2-methylsulfonylethyl]-4-acetylaminoisoindoline-1,3-dione potently inhibits PDE4 and TNF-α production, and exhibits modest inhibitory effects on LPS induced IL1β and IL12. L. G. Corral, et al., *Ann. Rheum. Dis.* 58:(Suppl I) 1107-1113 (1999). PDE4 is one of the major phosphodiesterase isoenzymes found in human myeloid and lymphoid lineage cells. The enzyme plays a crucial part in regulating cellular activity by degrading the ubiquitous second messenger cAMP and maintaining it at low intracellular levels. Id. Inhibition of PDE4 activity results in increased cAMP levels leading to the modulation of LPS induced cytokines including inhibition of TNF-α production in monocytes as well as in lymphocytes.

The (+) enantiomer of 2-[1-(3-ethoxy-4-methoxyphenyl)-2-methylsulfonylethyl]-4-acetylaminoisoindoline-1,3-dione can be prepared according to methods disclosed in U.S. Patent Application Publication No. 20030187052, titled "(+)-2-[1-(3-Ethoxy-4-methoxyphenyl)-2-methylsulfonylethyl]-4-acetylaminoisoindoline-1,3-dione: Methods Of Using And Compositions Thereof," having a filing date of Mar. 19, 2003, which is incorporated herein by reference.

Generally, racemic 2-[1-(3-ethoxy-4-methoxyphenyl)-2-methylsulfonylethyl]-4-acetylaminoisoindoline-1,3-dione can be readily prepared using the methods described in U.S. Pat. No. 6,020,358, which is incorporated herein by reference. The corresponding (+) enantiomer can be isolated from the racemic compound by techniques known in the art. Examples include, but are not limited to, the formation of chiral salts and the use of chiral or high performance liquid chromatography "HPLC" and the formation and crystallization of chiral salts. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N.Y., 1962); and Wilen, S. H., *Tables of Resolving Agents and Optical Resolutions* p. 268 (E. L. Eliel, Ed., Univ. of Notre Dame Press, Notre Dame, Ind., 1972).

In a specific method, the (+) enantiomer of 2-[1-(3-ethoxy-4-methoxyphenyl)-2-methylsulfonylethyl]-4-acetylaminoisoindoline-1,3-dione is synthesized from 3-acetamidophthalic anhydride and a chiral amino acid salt of (S)-2-(3-ethoxy-4-methoxyphenyl)-1-(methylsulphonyl)-eth-2-ylamine. Chiral amino acid salts of (S)-2-(3 ethoxy-4-methoxyphenyl)-1-(methylsulphonyl)-eth-2-ylamine include, but are not limited to salts formed with the L isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, ornithine, 4-aminobutyric acid, 2-aminoisobutyric acid, 3-aminopropionic acid, ornithine, norleucine, norvaline, hydroxyproline, sarcosine, citrulline, cysteic acid, t-butylglycine, t-butylalanine, phenylglycine, cyclohexylalanine, and N-acetyl-L-leucine. A specific chiral amino acid salt is (S)-2-(3-ethoxy-4-methoxyphenyl)-1-(methylsulphonyl)-eth-2-ylamine N-acetyl-L-leucine salt, which is resolved from 2-(3-ethoxy-4-methoxyphenyl)-1-(methylsulphonyl)-eth-2-ylamine and N-acetyl-L-leucine in methanol.

5.4 Pharmaceutical Compositions and Dosage Forms

Pharmaceutical compositions can be used in the preparation of individual, single unit dosage forms. Pharmaceutical compositions and dosage forms of the invention can comprise (+)-2-[1-(3-ethoxy-4-methoxyphenyl)-2-methylsulfonylethyl]-4-acetylaminoisoindoline-1,3-dione or a pharmaceutically acceptable salt or solvate thereof and a second active agent. Examples of the optional second active agents are disclosed herein (see, e.g., section 5.2.1). Pharmaceutical compositions and dosage forms of the invention can further comprise one or more carriers, excipients or diluents.

Single unit dosage forms of the invention are suitable for oral, mucosal (e.g., nasal, sublingual, vaginal, cystic, rectal, preputial, ocular, buccal or aural), parenteral (e.g., subcutaneous, intravenous, bolus injection, intramuscular or intraarterial), topical (e.g., eye drops or other ophthalmic preparations), transdermal or transcutaneous administration to a patient. Non-limiting examples of dosage forms include tablets; caplets; capsules, such as soft elastic gelatin capsules; cachets; troches; lozenges; dispersions; suppositories; powders; aerosols (e.g., nasal sprays or inhalers such as metered dose inhaler); gels; liquid dosage forms suitable for oral or mucosal administration to a patient, including suspensions (e.g., aqueous or non-aqueous liquid suspensions, oil-in-water emulsions or a water-in-oil liquid emulsions), solutions and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients can be accelerated by some excipients such as lactose or when exposed to water. Active ingredients that comprise primary or secondary amines are particularly susceptible to such accelerated decomposition. Consequently, this invention encompasses pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (USP) 25-NF20 (2002). In general, lactose-free compositions comprise active ingredients, a binder/filler and a lubricant in pharmaceutically compatible and pharmaceutically acceptable amounts. Particular lactose-free dosage forms comprise active ingredients, microcrystalline cellulose, pre-gelatinized starch and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Non-limiting examples of suitable packaging include hermetically sealed foils, plastics, unit dose containers (e.g., vials), blister packs and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers or salt buffers. Like the amounts and types of excipients, the amounts and specific types of active ingredients in a dosage form may differ depending on factors such as, but not limited to, the route by which it is to be administered to patients. However, typical dosage forms of the invention comprise the (+) enantiomer of 2-[1-(3-ethoxy-4-methoxyphenyl)-2-methylsulfonylethyl]-4-acetylaminoisoindoline-1,3-dione or a pharmaceutically acceptable salt or solvate thereof in an amount of from about 1 to about 1,000 mg. Typical dosage forms comprise the (+) enantiomer of 2-[1-(3-ethoxy-4-methoxyphenyl)-2-methylsulfonylethyl]-4-acetylaminoisoindoline-1,3-dione or a pharmaceutically acceptable salt or solvate thereof in an amount of about 1, 2, 5, 7.5, 10, 12.5, 15, 17.5, 20, 25, 50, 100, 150 or 200 mg. In a particular embodiment, a dosage form comprises the (+) enantiomer of 2-[1-(3-ethoxy-4-methoxyphenyl)-2-methylsulfonylethyl]-4-acetylaminoisoindoline-1,3-dione in an amount of about 1, 5, 10, 25, 50, 100 or 200 mg.

5.4.1 Oral Dosage Forms

Pharmaceutical compositions of the invention that are suitable for oral administration can be presented as discrete dosage forms, such as, but not limited to, tablets (e.g., chewable tablets), caplets, capsules and liquids (e.g., flavored syrups). Such dosage forms contain predetermined amounts of active ingredients and can be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. Non-limiting examples of excipients suitable for use in oral liquid or aerosol dosage forms include water, glycols, oils, alcohols, flavoring agents, preservatives and coloring agents. Non-limiting examples of excipients suitable for use in solid oral dosage forms (e.g., powders, tablets, capsules and caplets) include starches, sugars, micro-crystalline cellulose, diluents, granulating agents, lubricants, binders and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers or both and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Non-limiting examples of excipients that can be used in oral dosage forms of the invention include binders, fillers, disintegrants and lubricants. Non-limiting examples of binders suitable for use in pharmaceutical compositions and dosage forms include corn starch, potato starch or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose and mixtures thereof.

Non-limiting examples of suitable forms of microcrystalline cellulose include the materials sold as AVICEL-PH-101, AVICEL-PH-103 AVICEL RC-581, AVICEL-PH-105 (available from FMC Corporation, American Viscose Division, Avicel Sales, Marcus Hook, Pa.) and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Non-limiting examples of fillers suitable for use in the pharmaceutical compositions and dosage forms disclosed herein include talc, calcium carbonate (e.g., granules or powder), microcrystalline cellulose, powdered cellulose, dextrates, kaolin, mannitol, silicic acid, sorbitol, starch, pre-gelatinized starch and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation and is readily discernible to those of ordinary skill in the art. Typical pharmaceutical compositions comprise from about 0.5 to about 15 weight percent of disintegrant, preferably from about 1 to about 5 weight percent of disintegrant.

Non-limiting examples of disintegrants that can be used in pharmaceutical compositions and dosage forms of the invention include agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums and mixtures thereof.

Non-limiting examples of lubricants that can be used in pharmaceutical compositions and dosage forms of the invention include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laureate, agar and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.) and mixtures thereof. If used at all, lubricants are typically used in an amount of less than about 1 weight percent of the pharmaceutical compositions or dosage forms into which they are incorporated.

A particular solid oral dosage form of the invention comprises the (+) enantiomer of 2-[1-(3-ethoxy-4-methoxyphenyl)-2-methylsulfonylethyl]-4-acetylaminoisoindoline-1,3-dione, anhydrous lactose, microcrystalline cellulose, polyvinylpyrrolidone, stearic acid, colloidal anhydrous silica and gelatin.

5.4.2 Delayed Release Dosage Forms

Active ingredients of the invention can be administered by controlled release means or by delivery devices that are well known to those of ordinary skill in the art. Non-limiting examples of controlled release means or delivery devices include those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556 and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency and increased patient compliance. In addition, controlled-release formulations can be used to affect the time of onset of action or other characteristics, such as blood levels of the drug and can thus affect the occurrence of side (e.g., adverse) effects.

Most controlled-release formulations are designed to initially release an amount of drug (active ingredient) that promptly produces the desired therapeutic effect and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water or other physiological conditions or compounds.

5.4.3 Parenteral Dosage Forms

Parenteral dosage forms can be administered to patients by various routes including, but not limited to, subcutaneous, intravenous (including bolus injection), intramuscular and intraarterial. Because their administration typically bypasses patients' natural defenses against contaminants, parenteral dosage forms are preferably sterile or capable of being sterilized prior to administration to a patient. Non-limiting examples of parenteral dosage forms include solutions ready for injection, dry products ready to be dissolved or suspended in a pharmaceutically acceptable vehicle for injection, suspensions ready for injection and emulsions.

Suitable vehicles that can be used to provide parenteral dosage forms of the invention are well known to those skilled in the art. Non-limiting examples of suitable vehicles include Water for Injection USP; aqueous vehicles such as, but not limited to, Sodium Chloride Injection, Ringer's Injection, Dextrose Injection, Dextrose and Sodium Chloride Injection and Lactated Ringer's Injection; water-miscible vehicles such as, but not limited to, ethyl alcohol, polyethylene glycol and polypropylene glycol; and non-aqueous vehicles such as, but not limited to, corn oil, cottonseed oil, peanut oil, sesame oil, ethyl oleate, isopropyl myristate and benzyl benzoate.

Compounds that increase the solubility of one or more of the active ingredients disclosed herein can also be incorporated into the parenteral dosage forms of the invention. For example, cyclodextrin and its derivatives can be used to increase the solubility of the (+) enantiomer of 2-[1-(3-ethoxy-4-methoxyphenyl)-2-methylsulfonylethyl]-4-acetylaminoisoindoline-1,3-dione and its derivatives.

5.4.4 Topical and Mucosal Dosage Forms

Drugs can be applied locally to the skin and its adnexa or to a variety of mucous membranes. The routes that can be used include nasal, sublingual, vaginal, cystic, rectal, preputial, ocular, buccal or aural. Many dosage forms have been developed to deliver active principles to the site of application to produce local effects. Non-limiting examples of topical and mucosal dosage forms of the invention include sprays, inhalers, aerosols, ointments, creams, gels, pastes, dusting powders, lotions, liniments, poultices, solutions, emulsions, suspensions, eye drops or other ophthalmic preparations or other forms known to one of skill in the art. See, e.g., *Remington's Pharmaceutical Sciences*, $16^{th}$ and $18^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts and depend on the particular tissue to which a given pharmaceutical composition or dosage form will be applied. Non-limiting examples of typical excipients include water, acetone, ethanol, ethylene glycol, propylene glycol, butane-1,3-diol, isopropyl myristate, isopropyl palmitate, mineral oil and mixtures thereof to form solutions, emulsions or gels, which are non-toxic and pharmaceutically acceptable.

Moisturizers such as occlusives, humectants, emollients and protein rejuvenators can also be added to pharmaceutical compositions and dosage forms if desired. Examples of such additional ingredients are well known in the art. See, e.g., *Remington's Pharmaceutical Sciences*, $16^{th}$ and $18^{th}$ eds., Mack Publishing, Easton Pa. (1980 & 1990).

Occlusives are substances that physically block water loss in the stratum corneum. Non-limiting examples of occlusives include petrolatum, lanolin, mineral oil, silicones such as dimethicone, zinc oxide and combinations thereof. Preferably, the occlusives are petrolatum and lanolin, more preferably petrolatum in a minimum concentration of 5%.

Humectants are substances that attract water when applied to the skin and theoretically improve hydration of the stratum corneum. However, the water that is drawn to the skin is water from other cells, not atmospheric water. With this type of moisturizer, evaporation from the skin can continue and actually can make the dryness worse. Non-limiting examples of humectants include glycerin, sorbitol, urea, alpha hydroxy acids, sugars and combinations thereof. Preferably, the humectants are alpha hydroxy acids, such as glycolic acid, lactic acid, malic acid, citric acid and tartaric acid.

Emollients are substances that smooth skin by filling spaces between skin flakes with droplets of oil, and are not usually occlusive unless applied heavily. When combined with an emulsifier, they may help hold oil and water in the stratum corneum. Vitamin E is a common additive, which appears to have no effect, except as an emollient. Likewise, other vitamins, for example, A and D, are also added, but their effect is questionable. Non-limiting examples of emollients include mineral oil, lanolin, fatty acids, cholesterol, squalene, structural lipids and combinations thereof.

Protein rejuvenators are substances that rejuvenate the skin by replenishing essential proteins. Non-limiting examples of protein rejuvenators include collagen, keratin, elastin and combinations thereof.

The pH of a pharmaceutical composition or dosage form may also be adjusted to improve delivery of one or more active ingredients. Similarly, the polarity of a solvent carrier, its ionic strength or tonicity can be adjusted to improve delivery. For example, absorption through the skin can also be enhanced by occlusive dressings, inunction or the use of dimethyl sulfoxide as a carrier. Compounds such as metal stearates (e.g., calcium stearate, zinc stearate, magnesium stearate, sodium stearate, lithium stearate, potassium stearate, etc.) can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant and as a delivery-enhancing or penetration-enhancing agent. Different salts, hydrates or solvates of the active ingredients can be used to further adjust the properties of the resulting composition.

5.5 Dosages

Toxicity and therapeutic efficacy of the compound of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of the compound lies preferably within a range of circulating concentrations that include the $ED_{50}$ with little or no toxicity. The dosage may vary within this range depending upon the dosage form employed and the route of administration utilized. For any compound used in the method of the invention, the therapeutically sufficient dose can be estimated initially from cell culture assays. A dose can be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

In one embodiment of the invention, (+)-2-[1-(3-ethoxy-4-methoxyphenyl)-2-methylsulfonylethyl]-4-acetylaminoisoindoline-1,3-dione can be administered orally and in single or divided daily doses in an amount of from about 1 to about 1,000 mg/day. In a particular embodiment, (+)-2-[1-(3-ethoxy-4-methoxyphenyl)-2-methylsulfonylethyl]-4-acetylaminoisoindoline-1,3-dione can be administered in an amount of from about 5 to about 500 mg per day, or from about 10 to about 200 mg every day. Alternatively, the daily dose of the (+) enantiomer of 2-[1-(3-ethoxy-4-methoxyphenyl)-2-methylsulfonylethyl]-4-acetylaminoisoindoline-1,3-dione is from about 0.01 mg to about 100 mg per kg of a body weight of a patient.

The amount of the pharmaceutical composition administered according to the methods of the invention will depend on the subject being treated, the severity of the disorder or symptom of the disorder, the manner of administration, the frequency of administration and the judgment of the prescribing physician.

The frequency of administration is in the range of about an hourly dose to a monthly dose. In specific embodiments, administration is from 8 times per day to once every other day, or from 1 to 4 times per day. In a specific embodiment, a pharmaceutical composition of the invention is administered chronically, e.g., daily.

6. EXAMPLES

Some embodiments of the invention are illustrated by the following non-limiting examples. The examples should not be construed as a limitation in the scope thereof. The scope of the invention is defined solely by the appended claims.

6.1 Example 1

SYNTHESIS OF 2-[1-(3-ETHOXY-4-METHOXYPHENYL)-2-METHYLSULFONYLETHYL]-4-ACETYLAMINOISOINDOLINE-1,3-DIONE

A stirred solution of 1-(3-ethoxy-4-methoxyphenyl)-methylsulfonylethylamine (1.0 g, 3.7 mmol) and 3-acetamidophthalic anhydride (751 mg, 3.66 mmol) in acetic acid (20 mL) was heated at reflux for 15 h. The solvent was removed in vacuo to yield an oil. Chromatography of the resulting oil yielded the product as a yellow solid (1.0 g, 59% yield): mp, 144° C.; $^1$H NMR (CDCl$_3$) $\delta$1.47 (t, J=7.0 Hz, 3H, CH$_3$), 2.26 (s, 3H, CH$_3$), 2.88 (s,3H, CH$_3$), 3.75 (dd, J=4.4, 14.3 Hz, 1H, CHH) 3.85 (s, 3H, CH3), 4.11 (q, J=7 Hz, 2H, CH2), 5.87 (dd, J=4.3, 10.5 Hz, 1H, NCH), 6.82-6.86 (m, 1H, Ar), 7.09-7.11 (m, 2H, Ar), 7.47 (d, J=7 Hz, 1H, Ar), 7.64 (t, J=8 Hz, 1H, Ar), 8.74 (d, J=8 Hz, 1H, Ar), 9.49 (br s, 1H, NH); $^{13}$C NMR (CDCl$_3$) $\delta$14.61, 24.85, 41.54, 48.44, 54.34, 55.85, 64.43, 111.37, 112.34, 115.04, 118.11, 120.21, 124.85, 129.17, 130.96, 136.01, 137.52, 148.54, 149.65, 167.38, 169.09, 169.40; Anal Calc'd. for C$_{22}$H$_{24}$NO$_7$S: C, 57.38; H, 5.25; N, 6.08. Found: C, 57.31; H, 5.34; N, 5.83.

6.2 Example 2

PREPARATION OF (+)-2-[1-(3-ETHOXY-4-METHOXYPHENYL)-2-METHYLSULFONYL-ETHYL]-4-ACETYLAMINOISOINDOLINE-1,3-DIONE

Preparation of 3-Aminophthalic acid. A mixture of 10% Pd/C (2.5 g), 3-nitrophthalic acid (75.0 g, 355 mmol) and ethanol (1.5 L) was charged to a 2.5 L Parr hydrogenator, under a nitrogen atmosphere. Hydrogen was charged to the reaction vessel for up to 55 psi. The mixture was shaken for 13 hours, maintaining hydrogen pressure between 50 and 55 psi. Hydrogen was released and the mixture was purged with nitrogen 3 times. The suspension was filtered through a celite bed and rinsed with methanol. The filtrate was concentrated in vacuo. The resulting solid was reslurried in ether and isolated by vacuum filtration. The solid was dried in vacuo to a constant weight, affording 54 g (84% yield) of 3-aminopthalic acid as a yellow product. $^1$H-NMR (DMSO-d6) $\delta$: 3.17 (s, 2H), 6.67 (d, 1H), 6.82 (d, 1H), 7.17 (t, 1H), 8-10 (brs, 2H). $^{13}$C-NMR(DMSO-d6)$\delta$: 112.00, 115.32, 118.20, 131.28, 135.86, 148.82, 169.15, 170.09.

Preparation of 3-acetamidophthalic anhydride. A 1 L 3-necked round bottom flask was equipped with a mechanical stirrer, thermometer, and condenser and charged with 3-aminophthalic acid (108 g, 596 mmol) and acetic anhydride (550 mL). The reaction mixture was heated to reflux for 3 hours and cooled to ambient temperature and further to 0-5° C. for another 1 hour. The crystalline solid was collected by vacuum filtration and washed with ether. The solid product was dried in vacua at ambient temperature to a constant weight, giving 75 g (61% yield) of 3-acetamidopthalic anhydride as a white product. $^1$H-NMR(CDCl$_3$)$\delta$: 221 (s, 3H), 7.76 (d, 1H), 7.94 (t, 1H), 8.42 (d, 1H), 9.84 (s, 1H).

Resolution of 2-(3-ethoxy-4-methoxyphenyl)-1-(methylsulphonyl)-eth-2-ylamine. A 3 L 3-necked round bottom flask was equipped with a mechanical stirrer, thermometer, and condenser and charged with 2-(3-ethoxy-4-methoxyphenyl)-1-methylsulphonyl)-eth-2-ylamine (137.0 g 500 mmol), N-acetyl-L-leucine (52 g, 300 mmol), and methanol (1.0 L). The stirred slurry was heated to reflux for 1 hour. The stirred mixture was allowed to cool to ambient temperature and stirring was continued for another 3 hours at ambient temperature. The slurry was filtered and washed with methanol (250 L). The solid was air-dried and then dried in vacuo at ambient temperature to a constant weight, giving 109.5 g (98% yield) of the crude product (85.8% ee). The crude solid (55.0 g) and methanol (440 mL) were brought to reflux for 1 hour, cooled to room temperature and stirred for an additional 3 hours at ambient temperature. The slurry was filtered and the filter cake was washed with methanol (200 mL). The solid was air-dried and then dried in vacuo at 30° C. to a constant weight, yielding 49.6 g (90% recovery) of (S)-2-(3-ethoxy-4-methoxyphenyl)-1-(methylsulphonyl)-eth-2-ylamine-N-acetyl-L-leucine salt (98.4% ee). Chiral HPLC (1/99 EtOH/20 mM KH2PO4 @pH 7.0, Ultron Chiral ES-OVS from Agilent Technologies, 150 mm×4.6 mm, 0.5 mL/min., @240 nm): 18.4 min (S-isomer, 99.2%), 25.5 min (R-isomer, 0.8%).

Preparation of (+)-2-[1-(3-Ethoxy-4-methoxyphenyl)-2-methylsulfonylethyl]-4-acetylaminoisoindoline-1,3-dione. A 500 mL 3-necked round bottom flask was equipped with a mechanical stirrer, thermometer, and condenser. The reaction vessel was charged with (S)-2-(3-ethoxy-4-methoxyphenyl)-1-(methylsulphonyl)-eth-2-yl amine N-acetyl-L-leucine salt (25 g, 56 mmol, 98% ee), 3-acetamidophthalic anhydride (12.1 g 58.8 mmol), and glacial acetic acid (250 mL). The mixture was refluxed over night and then cooled to <50° C. The solvent was removed in vacuo, and the residue was dissolved in ethyl acetate. The resulting solution was washed with water (250 mL×2), saturated aqeous NaHCO$_3$ (250 mL×2), brine (250 mL×2), and dried over sodium sulphate. The solvent was evaporated in vacuo, and the residue recrystallized from a binary solvent containing ethanol (150 mL) and acetone (75 mL). The solid was isolated by vacuum filtration and washed with ethanol (100 mL×2). The product was dried in vacuo at 60° C. to a constant weight, affording 19.4 g (75% yield) of (S)-{2-[1-(3-ethoxy-4-methoxyphenyl)-2-methylsulfonylethyl]-4-inoisoindoline-1,3-dione with 98% ee. Chiral HPLC (15/85 EtOH/20 mM KH$_2$PO$_4$ @pH 0.5, Ultron Chiral ES-OVS from Agilent Technology, 150 mm×4.6 mm, 0.4 mL/min., @240 nm): 25.4 min (S-isomer, 98.7%), 29.5 min (R-isomer, 1.2%). $^1$H-NMR (CDCl$_3$) $\delta$: 1.47 (t, 3H), 2.26 (s, 3H), 2.87 (s, 3H), 3.68-3.75 (dd, 1H), 3.85 (s, 3H), 4.07-4.15 (q, 2H), 4.51-4.61 (dd, 1H), 5.84-5.90 (dd, 1H), 6.82-8.77 (m, 6H), 9.46 (s, 1H). $^{13}$C-NMR (DMSO-d6) δ: 14.66, 24.92, 41.61, 48.53, 54.46, 55.91, 111.44, 112.40, 115.10, 118.20, 120.28, 124.94, 129.22, 131.02, 136.09, 137.60, 148.62, 149.74, 167.46, 169.14, 169.48.

6.3 Example 3

Treatment of Exercise-Induced Asthma

Phase II clinical study was performed to examine efficacy, safety, pharmacokinetic, pharmacodynamic effects of the (+) enantiomer of 2-[1-(3-ethoxy-4-methoxyphenyl)-2-methylsulfonylethyl]-4-acetylaminoisoindoline-1,3-dione.

Four to 28 days prior to the start of the study medication, screening procedures were performed with male patients ≧18 and ≦45 years of age with a history of exercise-induced asthma and a history of at least one year of mild stable asthma ($FEV_1$ ≧70% predicted normal value) who required only short-acting β-agonists for routine asthma control. One screening and one baseline exercise-challenge test took place during the 28-day pre-randomization phase. After screening, twenty six and twenty three patients were administrated with (+) enantiomer of the invention in an amount of about 20 mg once daily (QD) or twice daily (BID), respectively, for 29 days. Twenty four subjects received placebo for 29 days.

In the study, the efficacy of the (+) enantiomer of the invention was examined in improving (i.e., reducing) the percentage fall in forced expiratory volume in 1 second ($FEV_1$) following exercise-challenge testing in subjects with mild asthma. The primary efficacy variable was maximum post exercise percentage fall index (% FI) at Day 29 and was calculated as follows:

$$\% FI = \frac{\text{preexercise } FEV_1 - \text{lowest } FEV_1 (\text{after excercise})}{\text{preexercise } FEV_1} \times 100$$

The (+) enantiomer of the invention at doses of 20 mg QD and 20 mg BID showed 4.6% and 10.0% improvements, respectively, in maximum post exercise % FI compared to baseline at Day 29, while placebo group showed -6.4%.

The pharmacodynamic studies included absolute change in resting AM online measurements of exhaled nitric oxide on Days 1, 15, and 29; ex vivo LPS-stimulated TNF-α levels measurements in whole blood on Days 1 and 29; and whole blood gene expression (mRNA) analysis of inflammatory mediators on Days 1 and 29.

Subjects treated with the (+) enantiomer had greater mean reductions from baseline in exhaled nitric oxide than placebo. Mean percent reductions from baseline in exhaled nitric oxide were 17.8% (20 mg QD), 16.0% (20 mg BID) and 7.1% (placebo) at Day 15; and 21.9% (20 mg QD), 17.5% (20 mg BID) and 1.6% (placebo) at Day 29.

The (+) enantiomer of the invention inhibited whole blood LPS-stimulated TNF-α production ex vivo, whereas placebo caused an apparent stimulation of LPS-stimulated TNF-α production. Mean percent change whole blood TNF (2 hour post dose time point) is shown in Table 1 below. These results confirm a positive correlation between LPS-stimulated TNF-α inhibition and (+) enantiomer of the invention that was observed in pharmacokinetic/pharmacodynamic modeling studies.

TABLE 1

Mean percent change whole blood TNF

| Visit | 20 mg QD (n = 12) | 20 mg BID (n = 11) | Placebo (n = 13) |
|---|---|---|---|
| Day 1 | -40 | -29 | +25 |
| Day 29 | -17 | -28 | +13 |

For pharmacokinetic study, area under the concentration versus time curve (AUC), maximum concentration (Cmax), terminal elimination half-life ($t_{1/2}$), time to maximum concentration (Tmax), apparent clearance (CL/F), volume of distribution ($V_d$), and relative accumulation rate (RA) were measured. The summary of pharmacokinetic parameters is shown in Table 2 below.

TABLE 2

Summary of Pharmacokinetic Parameters in Asthma Patients (Preliminary Data)

| | Dose of (+) Enantiomer | | | |
|---|---|---|---|---|
| | 20 mg QD (n = 5) | | 20 mg BID (n = 4) | |
| Parameter[##] (unit) | Day 1 | Day 29 | Day 1 | Day 29[#] |
| $C_{max}$ (ng/ml)* | 242 (23.2) | 271 (19.7) | 252 (38.4) | 389 (17.8) |
| $t_{max}$ (h)** | 3.0 (2-3) | 3.0 (1-3) | 2.5 (2-3) | 1.5 (1-3) |
| $AUC_{0-12}$ (h · ng/ml)* | 1733 (17.7) | 1826 (31.6) | 1596 (43.8) | 2850 (17.30) |
| $AUC_{0-24}$ (h · ng/ml)* | 2199 (16.6) | 2169 (32.5) | NA | 3270 (17.30) |
| t ½ (hr)* | 5.1 (14.5) | 5.3 (36.2) | 3.8 (15.7) | 4.4 (29.1) |
| CL/F (mL/hr)* | 8670 (16.6) | 8775 (32.6) | 10902 (40.6) | 5952 (18.3) |
| Vz/F (mL)* | 63716 (20.0) | 67652 (45.2) | 59272 (52.6) | 37805 (26.7) |

*Geometric mean (geometric CV %)
** Median (min, max)
[#]Only a single 20 mg dose was administered on Day 29.
[##]Chiral Assay Safety study included observations of adverse events; clinical laboratory evaluations, e.g., urinalysis, chemistry, hematology including absolute white blood cell counts and anti-nuclear antibody; physical examination findings; vital sign measurements; 12-lead electrocardiogram recordings; and global assessment of atopic dermatitis (for subjects with atopic dermatitis at screening). The (+) enantiomer of the invention showed good tolerability at 20 mg given in a single dose or two divided doses per day. Dose-limiting adverse events were not observed. In particular, there was no dose-limiting nausea and no reported incidences of vomiting. None of the observed clinical laboratory parameter changes were considered to be clinically significant. There were no clinically relevant changes in vital sign measurements or ECG findings during the study. There were no unusual or unexpected safety findings. Overall, doses of 20 mg QD and 20 mg BID administration of (+) enantiomer were safe.

The results of these studies suggest that (+) enantiomer of 2-[1-(3-ethoxy-4-methoxyphenyl)-2-methylsulfonylethyl]-4-acetylaminoisoindoline-1,3-dione is a promising new agent for treating exercise-induced asthma.

6.4 Example 4

Experiment with a Murine Model of Ovalbumin-Induced Asthma

Activities of (+)-2-[1-(3-ethoxy-4-methoxyphenyl)-2-methylsulfonylethyl]-4-acetylaminoisoindoline-1,3-dione ("(+) isomer") for the treatment of exercise-induced asthma were investigated in a murine model of ovalbumin (OVA)-induced asthma. The effects on airway hyperresponsiveness (AHR), cellular infiltrate into the BAL and tissue, plasma total IgE levels, whole lung cytokine levels, and goblet cell hyperplasia in OVA-sensitized mice were assessed in this study.

Male BALB/c mice were sensitized to ovalbumin (OVA) via subcutaneous, intraperitoneal, intranasal and intratracheal routes. Animals were dosed with vehicle (0.5% carboxymethyl-cellulose (CMC)/0.25% Tween 80; p.o.), Budesonide (10 mg/kg; p.o.) or (+)-2-[1-(3-ethoxy-4-methoxyphenyl)-2-methylsulfonylethyl]-4-acetylaminoisoindoline-1,3-dione (1, 10 or 25 mg/kg; q.d.; p.o.) prior to intratracheal challenge with OVA until the end of the study.

Airway hyper-responsiveness (AHR) to methacholine (MCh, 3 mg/kg; i.v.), bronchoalveolar lavage total white blood cell and differential counts, total plasma IgE, whole-lung eotaxin, RANTES and IL-4 protein levels, and goblet cell hyperplasia were assessed 24, 48 and 72 hours after the second intratracheal OVA challenge. The model was set up as depicted in FIG. 1. (+)-2-[1-(3-Ethoxy-4-methoxyphenyl)-2-methylsulfonylethyl]-4-acetylaminoisoindoline-1,3-dione (1, 10 and 25 mg/kg) attenuated AHR at all timepoints measured (24 hour for 1, 10 and 25 mg/kg; 48 and 72 hours for 10 mg/kg). Total white blood cell counts were significantly attenuated by (+)-2-[1-(3-ethoxy-4-methoxyphenyl)-2-methylsulfonylethyl]-4-acetylaminoisoindoline-1,3-dione at 48 and 72 hours but not 24 hour after OVA challenge, with eosinophils and lymphocytes being the major cell types affected. Attenuation of subepithelial eosinophilia was also observed at 48 and 72 hours post-treatment. Total plasma IgE was decreased by (+)-2-[1-(3-ethoxy-4-methoxyphenyl)-2-methylsulfonylethyl]-4-acetylaminoisoindoline-1,3-dione (10 mg/kg) at 24 and 72 hours. Whole lung RANTES and eotaxin levels were decreased by (+)-2-[1-(3-ethoxy-4-methoxyphenyl)-2-methylsulfonylethyl]-4-acetylaminoisoindoline-1,3-dione (10 mg/kg) compared with vehicle control at 24, 48 and 72 hours. IL-4 levels were decreased at 24 and 48 hours. A significant attenuation of goblet cell hyperplasia was observed with (+)-2-[1-(3-ethoxy-4-methoxyphenyl)-2-methylsulfonylethyl]-4-acetylaminoisoindoline-1,3-dione at 24, 48 and 72 hours.

Airway Hyper-responsiveness. A significant increase in AHR was measured 24, 48 and 72 hours following OVA challenge in OVA-sensitized mice compared with naïve mice. Treatment with (+)-2-[1-(3-ethoxy-4-methoxyphenyl)-2-methylsulfonylethyl]-4-acetylaminoisoindoline-1,3-dione at 1 and 25 mg/kg or Budesonide (10 mg/kg) significantly attenuated MCh-induced AHR ($p<0.01$) compared to vehicle control, 24 h post OVA challenge (FIG. 2a). (+)-2-[1-(3-Ethoxy-4-methoxyphenyl)-2-methylsulfonylethyl]-4-acetylaminoisoindoline-1,3-dione at 10 mg/kg also significantly attenuated AHR 24, 48 and 72 h post OVA challenge ($p<0.01$, $p<0.01$ and $p<0.05$ respectively; FIG. 2b).

Total White Cell and Differential BAL Counts. A significant increase in total white blood cell counts was measured 24 h following OVA challenge in OVA-sensitized compared to naïve mice ($p<0.01$). Budesonide (10 mg/kg) significantly attenuated the increase in total white blood cell counts at this timepoint ($p<0.01$). However, (+)-2-[1-(3-ethoxy-4-methoxyphenyl)-2-methylsulfonylethyl]-4-acetylaminoisoindoline-1,3-dione at both 1 and 25 mg/kg had no effect on total white blood cell counts (FIGS. 3a and b). At later timepoints, 48 and 72 h post OVA challenge, a significant decrease ($p<0.05$) in total white blood cell counts was measured in the (+)-2-[1-(3-ethoxy-4-methoxyphenyl)-2-methylsulfonyleth]-4-acetylaminoisoindoline-1,3-dione (10 mg/kg) group compared to vehicle controls (FIG. 3b).

Following treatment with (+)-2-[1-(3-ethoxy-4-methoxyphenyl)-2-methylsulfonylethyl]-4-acetylaminoisoindoline-1,3-dione, a significant ($p<0.001$) increase in total BAL neutrophils was observed 24 h post OVA challenge. However, neutrophil numbers in the BAL returned to baseline levels at 48 and 72 h post OVA (FIG. 4a). An increase in total BAL eosinophil and lymphocyte numbers were measured 24, 48 and 72 h post OVA challenge in the vehicle group which were attenuated by (+)-2-[1-(3-ethoxy-4-methoxyphenyl)-2-methylsulfonylethyl]-4-acetylaminoisoindoline-1,3-dione (10 mg/kg) at these time points (FIGS. 4b and c). Macrophage numbers increased in the vehicle-treated group at 24, 48 and 72 h compared to naive mice, while (+)-2-[1-(3-ethoxy-4-methoxyphenyl)-2-methylsulfonylethyl]-4-acetylaminoisoindoline-1,3-dione treatment attenuated macrophage numbers at 48 and 72 h, but not 24 h (FIG. 4d).

Plasma IgE Levels. The time course of total IgE in the plasma was measured by ELISA. An increase in IgE levels in the vehicle control group was seen at 24 and 72 h (FIG. 5). Pre-treatment with (+)-2-[1-(3-ethoxy-4-methoxyphenyl)-2-methylsulfonylethyl]-4-acetylaminoisoindoline-1,3-dione caused a decrease in total IgE levels at 24 and 72 h compared with vehicle control group (FIG. 5).

Time Course of Whole Lung Cytokine Levels. RANTES, IL-4 and eotaxin were measured by ELISA in whole lung homogenates. Twenty-four, 48 and 72 h following OVA sensitization, an increase in RANTES and eotaxin levels was measured in the lung (FIGS. 6a and b, respectively) which was attenuated by pre-treatment with (+)-2-[1-(3-ethoxy-4-methoxyphenyl)-2-methylsulfonylethyl]-4-acetylaminoisoindoline-1,3-dione (FIGS. 6a and b). An increase in whole lung IL-4 levels was measured in vehicle treated-OVA-sensitized mice 24 and 48 h post OVA challenge, which returned to baseline levels at 72 h. (+)-2-[1-(3-Ethoxy-4-methoxyphenyl)-2-methylsulfonylethyl]-4-acetylaminoisoindoline-1,3-dione decreased the IL-4 levels at 24 and 48 h post OVA challenge (FIG. 6c).

Time Course of PAS-Positive Airways. PAS (Periodic Acid Schiff) staining was used to detect mucosubstances produced by goblet cells within the airways. PAS staining was carried out on 5 µM sections according to the manufacturers instructions using the PAS staining kit (Polysciences, PA). Twenty airways per section were counted and the PAS positive airways were expressed as a % of the total airways counted.

Following sensitization with OVA, an increase in the number of PAS-positive stained airways was observed (FIG. 7) as assessed by histology. Pre-treatment with (+)-2-[1-(3-ethoxy-4-methoxyphenyl)-2-methylsulfonylethyl]-4-acetylaminoisoindoline-1,3-dione (10 mg/kg) caused a significant ($p<0.05$) attenuation of the number of PAS-positive airways at all timepoints measured (FIG. 7).

Time Course of Subepithelial Eosinophilia. An increase in the number of subepithelial eosinophils was observed at 24, 48 and 72 h following sensitization of mice with OVA (FIG. 8). Significant abrogation of subepithelial eosinophilia was observed at 48 and 72 h (p<0.01 and p<0.05 respectively) following pre-treatment with (+)-2-[1-(3-ethoxy-4-methoxyphenyl)-2-methylsulfonylethyl]-4-acetylaminoisoindoline-1,3-dione (10 mg/kg; FIG. 8).

6.5 Example 5

Experiment in Guinea Pig Trachea

The effect of (+)-2-[1-(3-ethoxy-4-methoxyphenyl)-2-methylsulfonylethyl]-4-acetylaminoisoindoline-1,3-dione on guinea pig trachea under spontaneous tone contraction was assessed in this study.

The methods employed in this study have been adapted from the scientific literature to maximize reliability and reproducibility. See, Wasserman, M. A., et al., "Thromboxane B2-comparative bronchoactivity in experimental systems" *Eur. J. Pharmacol.* 46: pages 303-313 (1977). Male guinea pigs of the Hartley strain (700-900 g) were sacrificed by a blow on the head. The trachea was carefully dissected out and transferred to a dish containing Krebs-Henseleit solution. A wooden applicator stick of appropriate diameter was inserted longitudinally through the hollow trachea and the tissue cut spirally with a sharp scalpel to produce a thin continuous strip of tracheal tissue (2-3 segments of cartilage separated each turn of the spiral). Each strip was affixed to a pin in a 10-ml glass organ-bath, which was filled with Krebs-Henseleit solution. The temperature of the bath fluid was maintained constant at 37° C. and gassed with a 95% $O_2$-5% $CO_2$ mixture. The pH of the solution equilibrated with the gas mixture was 7.4. Each tissue was attached to a force displacement transducer (Grass FF-03) for monitoring isometric contractions. The responses were recorded on a Grass Model 5D polygraph. The tracheal strips were subjected to an initial base tension of 2 g and allowed to stabilize in the bath for 60 min. During this period, the bath fluid was changed several times. The compound was added only after this initial period of stabilization. The concentrations of the compound are expressed as the final molar concentration (M) in the bath fluid. The degree of contraction was assessed by measuring the pen excursion (mm) after instillation of a drug into the bath. The baths were washed thoroughly by overflow after each concentration of the compound. The tissues were permitted to rest at least 10 min between drug concentrations. The compound was examined in 6-9 tissues and $\log_{10}$ concentration-response curves were constructed. Mean $EC_{15mm}$±S.E. values (effective concentration of the compound which evokes a 15 mm contraction upon administration) were obtained after fitting by eye the best straight line through all points on each curve and then averaging the resultant values.

(+)-2-[1-(3-Ethoxy-4-methoxyphenyl)-2-methylsulfonylethyl]-4-acetylaminoisoindoline-1,3-dione induced smooth muscle relaxation, which could lead to direct bronchial dilation. The significant relaxation was observed for the compound with estimated $IC_{50}$ values of 310 nM. Concentration response curve is shown in FIG. 9.

6.6 Example 6

TNF-Alpha Inhibition

Human Whole Blood LPS-induced TNF-α assay. The ability of (+)-2-[1-(3-Ethoxy-4-methoxyphenyl)-2-methylsulfonylethyl]-4-acetylaminoisoindoline-1,3-dione ("(+) isomer") to inhibit LPS-induced TNF-α production by human whole blood was measured essentially as described below for the LPS-induced TNF-α assay in human PBMC, except that freshly drawn whole blood was used instead of PBMC. (George Muller, et al. 1999, *Bioorganic & Medicinal Chemistry Letters* 9; 1625-1630.) Human whole blood LPS-induced TNF-α $IC_{50}$=294 nM for (+) isomer; and 442 nM for racemate.

Mouse LPS-induced serum TNF-α inhibition. Compounds of (+) isomer and racemate were tested in this animal model according to previously described methods (Corral et al. 1996, *Mol. Med.* 2:506-515). Mouse LPS-induced serum TNF-α inhibition ($ED_{50}$, mg/kg, p.o.)=0.05 mg/kg for (+) isomer; and 1 mg/kg for racemate.

LPS-induced TNF-α production. Lipopolysaccharide (LPS) is an endotoxin produced by gram-negative bacteria such as *E. coli* which induces production of many pro-inflammatory cytokines, including TNF-α. In peripheral blood mononuclear cells (PBMC), the TNF-α produced in response to LPS is derived from monocytes, which comprise approximately 5-20% of the total PBMC. Compounds of (+) isomer and racemate were tested for the ability to inhibit LPS-induced TNF-α production from human PBMC as previously described (Muller et al. 1996, *J. Med. Chem.* 39:3238). PBMC from normal donors were obtained by Ficoll Hypaque (Pharmacia, Piscataway, N.J., USA) density centrifugation. Cells were cultured in RPMI (Life Technologies, Grand Island, N.Y., USA) supplemented with 10% AB±human serum (Gemini Bio-products, Woodland, Calif., USA), 2 mM L-glutamine, 100 U/ml penicillin, and 100 μg/ml streptomycin (Life Technologies).

PBMC ($2\times10^5$ cells) were plated in 96-well flat-bottom Costar tissue culture plates (Corning, N.Y., USA) in triplicate. Cells were stimulated with LPS (Sigma, St. Louis, Mo., USA) at 100 ng/ml in the absence or presence of compounds. Compounds of (+) isomer and racemate were dissolved in DMSO (Sigma) and further dilutions were done in culture medium immediately before use. The final DMSO concentration in all samples was 0.25%. Compounds were added to cells 1 hour before LPS stimulation. Cells were incubated for 18-20 hours at 37° C. in 5% $CO_2$ and supernatants were then collected, diluted with culture medium and assayed for TNF-α levels by ELISA (Endogen, Boston, Mass., USA). LPS-induced TNF-α $IC_{50}$=77 nM for (+) isomer; and 194 nM for racemate.

IL-1β-induced TNF-α production. During the course of inflammatory diseases, TNF-α production is often stimulated by the cytokine 1L-1β, rather than by bacterially derived LPS. Compounds of (+) isomer and racemate were tested for the ability to inhibit IL-1β-induced TNF-α production from human PBMC as described above for LPS-induced TNF-α production, except that the PBMC were isolated from source leukocyte units (Sera-Tec Biologicals, North Brunswick, N.J., USA) by centrifugation on Ficoll-Paque Plus (Amersham Pharmacia, Piscataway, N.J., USA), plated in 96-well tissue culture plates at $3\times10^5$ cells/well in RPMI-1640 medium (BioWhittaker, Walkersville, Md., USA) containing 10% heat-inactivated fetal bovine serum (Hyclone), 2 mM L-glutamine, 100 U/ml penicillin, and 100 mg/ml streptomycin (complete medium), pretreated with compounds at 10, 2, 0.4, 0.08, 0.016, 0.0032, 0.00064, and 0 μM in duplicate at a final DMSO concentration of 0.1% at 37° C. in a humidified incubator at 5% $CO_2$ for 1 hour, then stimulated with 50 ng/ml recombinant human IL-1β (Endogen) for 18 hours. IL-β-induced TNF-α $IC_{50}$=83 nM for (+) isomer; and 2,263 nM for racemate.

6.7 Example 7

PDE4 Inhibition

PDE4 (U937 cell-derived) enzyme assay. PDE4 enzyme was purified from U937 human monocytic cells by gel filtration chromatography as previously described (Muller et al. 1998, *Bioorg. & Med. Chem. Lett.* 8:2669-2674). Phosphodiesterase reactions were carried out in 50 mM Tris HCl pH 7.5, 5 mM $MgCl_2$, 1 μM cAMP, 10 nM [$^3$H]-cAMP for 30 min at 30° C., terminated by boiling, treated with 1 mg/ml snake venom, and separated using AG-1XS ion exchange resin (BioRad) as described (Muller et al. 1998, *Bioorg. & Med. Chem. Lett.* 8:2669-2674). Reactions consumed less than 15% of available substrate. PDE4 $IC_{50}$=73.5 nM for (+) isomer; and 81.8 nM for racemate.

6.8 Example 8

Aqueous Solubility

Equilibrium solubility was measured in pH 7.4 aqueous buffer. The pH 7.4 buffer was prepared by adjusting the pH of a 0.07 M $NaH_2PO_4$ solution to 7.4 with 10 N NaOH. The ionic strength of the solution was 0.15. At least 1 mg of powder was combined with 1 ml of buffer to make >1 mg/ml mixture. These samples were shaken for >2 hours and left to stand overnight at room temperature. The samples were then filtered through a 0.45-μm Nylon syringe filter that was first saturated with the sample. The filtrate was sampled twice, consecutively. The filtrate was assayed by HPLC against standards prepared in 50% methanol. (+)-2-[1-(3-Ethoxy-4-methoxyphenyl)-2-methylsulfonylethyl]-4-acetylaminoisoindoline-1,3-dione has 3.5-fold greater aqueous solubility than the racemic mixture. (Measured solubility of (+) isomer=0.012 mg/mL; and racemate=0.0034 mg/mL).

All of the references cited herein are incorporated by reference in their entirety. While the invention has been described with respect to the particular embodiments, it will be apparent to those skilled in the art that various changes and modifications can be made without departing from the spirit and scope of the invention as recited by the appended claims.

The embodiments of the invention described above are intended to be merely exemplary and those skilled in the art will recognize or will be able to ascertain using no more than routine experimentation, numerous equivalents of specific compounds, materials and procedures. All such equivalents are considered to be within the scope of the invention and are encompassed by the appended claims.

What is claimed is:

1. A method of treating exercise-induced asthma, which comprises administering to a patient in need of such treatment a therapeutically effective amount of (+)-2-[1-(3-ethoxy-4-methoxyphenyl)-2-methylsulfonylethyl]-4-acetylaminoisoindoline-1,3-dione, or a pharmaceutically acceptable salt or solvate thereof, substantially free of its (−) enantiomer.

2. The method of claim 1, wherein the patient is administered with (+)-2-[1-(3-ethoxy-4-methoxyphenyl)-2-methylsulfonylethyl]-4-acetylaminoisoindoline-1,3-dione having the formula:

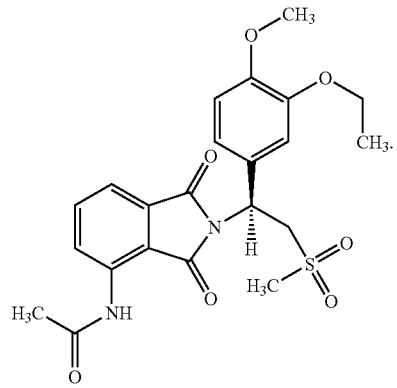

3. The method of claim 1, wherein the (+)-2-[1-(3-ethoxy-4-methoxyphenyl)-2-methylsulfonylethyl]-4-acetylaminoisoindoline-1,3-dione is administered as a pharmaceutically acceptable salt.

4. The method of claim 1, wherein the (+)-2-[1-(3-ethoxy-4-methoxyphenyl)-2-methylsulfonylethyl]-4-acetylaminoisoindoline-1,3-dione is administered as a pharmaceutically acceptable solvate.

5. The method of claim 4, wherein the (+)-2-[1-(3-ethoxy-4-methoxyphenyl)-2-methylsulfonylethyl]-4-acetylaminoisoindoline-1,3-dione is administered as a pharmaceutically acceptable hydrate.

6. The method of claim 1, wherein the (+)-2-[1-(3-ethoxy-4-methoxyphenyl)-2-methylsulfonylethyl]-4-acetylaminoisoindoline-1,3-dione or a pharmaceutically acceptable salt or solvate thereof is administered orally.

7. The method of claim 6, wherein the compound is administered in a dosage form of a tablet or a capsule.

8. The method of claim 1, wherein the (+)-2-[1-(3-ethoxy-4-methoxyphenyl)-2-methylsulfonylethyl]-4-acetylaminoisoindoline-1,3-dione or a pharmaceutically acceptable salt or solvate thereof is administered nasally.

9. The method of claim 8, wherein the compound is administered in a dosage form of an aerosol or a spray.

10. The method of claim 8, wherein the compound is administered via a metered dose inhaler.

11. The method of claim 1, wherein the therapeutically effective amount is from about 1 mg to about 1,000 mg per day.

12. The method of claim 11, wherein the therapeutically effective amount is from about 5 mg to about 500 mg per day.

13. The method of claim 12, wherein the therapeutically effective amount is from about 10 mg to about 200 mg per day.

14. The method of claim 1, wherein the therapeutically effective amount is from about 0.01 mg to about 100 mg per kg of a body weight of the patient per day.

15. The method of claim 14, wherein the therapeutically effective amount is about 1 mg, 10 mg or 25 mg per kg of a body weight of the patient per day.

* * * * *